(12) United States Patent
Eli et al.

(10) Patent No.: US 10,039,656 B2
(45) Date of Patent: Aug. 7, 2018

(54) COUPLED SCAFFOLD SEGMENTS

(71) Applicant: Abbott Cardiovascular Systems Inc., Santa Clara, CA (US)

(72) Inventors: Erik David Eli, Redwood City, CA (US); Syed Hossainy, Hayward, CA (US); Mikael Trollsas, San Jose, CA (US); Michael H. Ngo, San Jose, CA (US); Stephen Pacetti, San Jose, CA (US); Michael Green, Pleasanton, CA (US); John Papp, Temecula, CA (US)

(73) Assignee: ABBOTT CARDIOVASCULAR SYSTEMS INC., Santa Clara, CA (US)

( * ) Notice: Subject to any disclaimer, the term of this patent is extended or adjusted under 35 U.S.C. 154(b) by 810 days.

(21) Appl. No.: 13/910,998

(22) Filed: Jun. 5, 2013

(65) Prior Publication Data
US 2014/0364935 A1    Dec. 11, 2014

(51) Int. Cl.
| | | |
|---|---|---|
| *A61F 2/07* | (2013.01) | |
| *A61F 2/915* | (2013.01) | |
| *A61F 2/91* | (2013.01) | |
| *A61F 2/958* | (2013.01) | |
| *A61F 2/82* | (2013.01) | |

(52) U.S. Cl.
CPC .............. *A61F 2/915* (2013.01); *A61F 2/91* (2013.01); *A61F 2/958* (2013.01); *A61F 2002/828* (2013.01); *A61F 2002/91575* (2013.01); *A61F 2002/91591* (2013.01); *A61F 2210/0004* (2013.01); *A61F 2220/0075* (2013.01); *A61F 2220/0091* (2013.01)

(58) Field of Classification Search
CPC ...... A61F 2220/0025; A61F 2220/0091; A61F 2220/0007

USPC .............................. 623/1.11, 1.15, 1.16, 1.17
See application file for complete search history.

(56) References Cited

U.S. PATENT DOCUMENTS

| | | | | |
|---|---|---|---|---|
| 5,405,377 | A * | 4/1995 | Cragg | A61F 2/90 606/191 |
| 6,066,167 | A | 5/2000 | Lau et al. | |
| 8,414,528 | B2 | 4/2013 | Liu et al. | |
| 8,870,940 | B2 * | 10/2014 | Venturelli | A61F 2/91 623/1.15 |
| 2002/0111671 | A1 * | 8/2002 | Stenzel | A61F 2/91 623/1.16 |
| 2002/0120327 | A1 * | 8/2002 | Cox | A61F 2/07 623/1.16 |
| 2003/0135266 | A1 * | 7/2003 | Chew | A61F 2/915 623/1.16 |
| 2005/0125051 | A1 * | 6/2005 | Eidenschink | A61F 2/91 623/1.12 |

(Continued)

OTHER PUBLICATIONS

U.S. Appl. No. 13/840,257, Hossainy et al., filed Mar. 15, 2013.

(Continued)

*Primary Examiner* — Julie A Szpira
(74) *Attorney, Agent, or Firm* — Squire Patton Boggs (US) LLP

(57) ABSTRACT

A scaffold is formed by several segments joined or connected to each other by only at least one coupling. The coupling decouples the segments in the axial direction over a finite distance of axial displacement. The scaffold when implanted in a peripheral vessel reduces loading on rings of a segment due to the decoupling of the segments in the axial direction over the finite distance.

22 Claims, 19 Drawing Sheets

(56) References Cited

U.S. PATENT DOCUMENTS

| | | | |
|---|---|---|---|
| 2007/0142901 A1* | 6/2007 | Steinke | A61F 2/94 623/1.16 |
| 2007/0219612 A1* | 9/2007 | Andreas | A61B 17/12022 623/1.11 |
| 2008/0119943 A1* | 5/2008 | Armstrong | A61F 2/89 623/23.7 |
| 2009/0005848 A1* | 1/2009 | Strauss | A61F 2/91 623/1.2 |
| 2009/0030501 A1* | 1/2009 | Morris | A61F 2/915 623/1.15 |
| 2009/0228088 A1* | 9/2009 | Lowe | A61F 2/91 623/1.2 |
| 2011/0066222 A1* | 3/2011 | Wang | A61F 2/91 623/1.15 |
| 2011/0190872 A1 | 8/2011 | Anukhin et al. | |
| 2012/0042501 A1 | 2/2012 | Wang et al. | |
| 2013/0178926 A1* | 7/2013 | Denison | A61F 2/88 623/1.16 |

OTHER PUBLICATIONS

U.S. Appl. No. 13/644,347, Wang, filed Oct. 4, 2012.
U.S. Appl. No. 13/584,678, Hossainy et al., filed Aug. 13, 2012.
Angioplasty Summit Abstracts/Oral, The Am. J. of Cardiology, Apr. 23-26, 2013, p. 23B.
Bosiers et al., "Coronary and endovascular applications of the Absorb™ bioresorbable vascular scaffold", Interv. Cardiol. 4(6), pp. 621-631 (2012).
Miller "Abbott's Bioresorbable Stent Shows Durable Results in ABSORB Trial", The Gray Sheet, pp. 17-18, Mar. 2003.

* cited by examiner

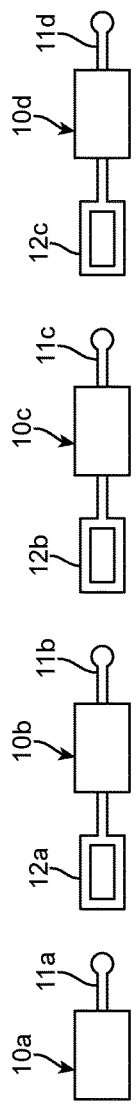
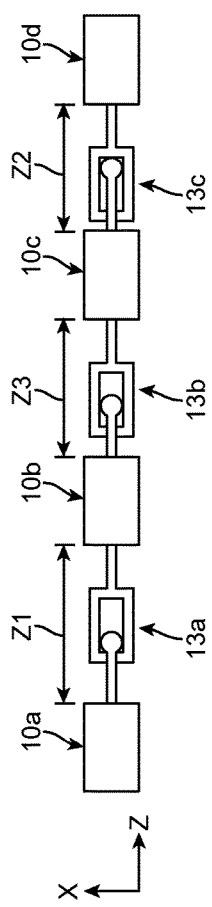
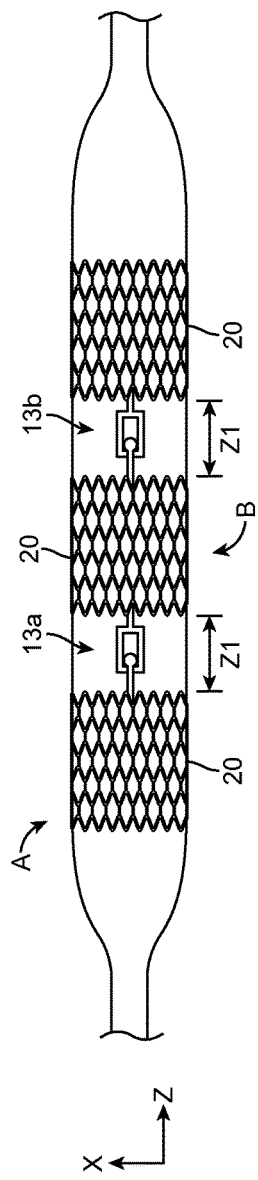

COUPLED SCAFFOLD SEGMENTS

BACKGROUND OF THE INVENTION

Field of the Invention

The present invention relates to bioresorbable scaffolds; more particularly, this invention relates to bioresorbable scaffolds for treating peripheral vessels of the body.

Description of the State of the Art

Radially expandable endoprostheses are artificial devices adapted to be implanted in an anatomical lumen. An "anatomical lumen" refers to a cavity, duct, of a tubular organ such as a blood vessel, urinary tract, and bile duct. Stents are examples of endoprostheses that are generally cylindrical in shape and function to hold open and sometimes expand a segment of an anatomical lumen (one example of a stent is found in U.S. Pat. No. 6,066,167 to Lau et al). Stents are often used in the treatment of atherosclerotic stenosis in blood vessels. "Stenosis" refers to a narrowing or constriction of the diameter of a bodily passage or orifice. In such treatments, stents reinforce the walls of the blood vessel and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

The treatment of a diseased site or lesion with a stent involves both delivery and deployment of the stent. "Delivery" refers to introducing and transporting the stent through an anatomical lumen to a desired treatment site, such as a lesion. "Deployment" corresponds to expansion of the stent within the lumen at the treatment region. Delivery and deployment of a stent are accomplished by positioning the stent about one end of a catheter, inserting the end of the catheter through the skin into an anatomical lumen, advancing the catheter in the anatomical lumen to a desired treatment location, expanding the stent at the treatment location, and removing the catheter from the lumen.

In the case of a balloon expandable stent, the stent is mounted about a balloon disposed on the catheter. Mounting the stent typically involves compressing or crimping the stent onto the balloon prior to insertion in an anatomical lumen. Crimping refers to an iris-type or other form of crimper, such as the crimping machine disclosed and illustrated in US 2012/0042501. At the treatment site within the lumen, the stent is expanded by inflating the balloon. The balloon may then be deflated and the catheter withdrawn from the stent and the lumen, leaving the stent at the treatment site. In the case of a self-expanding stent, the stent may be secured to the catheter via a retractable sheath. When the stent is at the treatment site, the sheath may be withdrawn which allows the stent to self-expand.

The stent must be able to satisfy a number of basic, functional requirements. The stent must be capable of withstanding the structural loads, for example, radial compressive forces, imposed on the stent as it supports the walls of a vessel after deployment. Therefore, a stent must possess adequate radial strength. After deployment, the stent must adequately maintain its size and shape throughout its service life despite the various forces that may come to bear on it. In particular, the stent must adequately maintain a vessel at a prescribed diameter for a desired treatment time despite these forces. The treatment time may correspond to the time required for the vessel walls to remodel, after which the stent is no longer necessary for the vessel to maintain a desired diameter.

A commonly used type of peripheral stent is the self-expanding stent made from super-elastic material, such as Nitinol. This type of material is known for its ability to return to its original configuration after severe deformation, such as a crushing load or longitudinal bending. However, this variety of self-expanding stents have undesired qualities; most notably, the high resiliency of super-elastic material produces what is commonly referred to as a "chronic outward force" (COF) on the blood vessel supported by the stent. Complications resulting from COF are discussed in Schwartz, Lewis B. et al. *Does Stent Placement have a learning curve: what mistakes do we as operators have to make and how can they be avoided?*, Abbott Laboratories; Abbott Park, Ill., USA. It is believed that a COF exerted on a blood vessel by a self-expending stent is a main contributor to high degrees of restenosis of lesions treated by the self-expanding stent. It has been shown that not even an anti-proliferative drug delivered from drug eluting self-expandable stents can mitigate the restenosis caused by the stent's COF. Stents that are plastically deformed by a balloon to support a vessel do not suffer from this drawback. Indeed, balloon expanded stents, in contrast to self-expanding stents made from a super-elastic material, have the desirable quality of being deployable to the desired diameter for supporting the vessel without exerting residual outward forces on the vessel.

A balloon-expanded polymer scaffold, such as that described in US 2010/0004735 is made from a biodegradable, bioabsorbable, bioresorbable, or bioerodable polymer. The terms biodegradable, bioabsorbable, bioresorbable, biosoluble or bioerodable refer to the property of a material or stent to degrade, absorb, resorb, or erode away from an implant site. The polymer scaffold described in US 2010/0004735, for example, as opposed to a metal stent, is intended to remain in the body for only a limited period of time. In many treatment applications, the presence of a stent in a body may be necessary for a limited period of time until its intended function of, for example, maintaining vascular patency and/or drug delivery is accomplished. Moreover, it has been shown that biodegradable scaffolds allow for improved healing of the anatomical lumen as compared to metal stents, which may lead to a reduced incidence of late stage thrombosis. In these cases, there is a desire to treat a vessel using a polymer scaffold, in particular a bioabsorable or bioresorbable polymer scaffold, as opposed to a metal stent, so that the prosthesis's presence in the vessel is for a limited duration. However, there are numerous challenges to overcome when developing a polymeric scaffold.

The art recognizes a variety of factors that affect a polymeric scaffold's ability to retain its structural integrity and/or shape when subjected to external loadings, such as crimping and balloon expansion forces. These interactions are complex and the mechanisms of action not fully understood. According to the art, characteristics differentiating a polymeric, bioresorbable scaffold of the type expanded to a deployed state by plastic deformation from a similarly functioning metal scaffold are many and significant. Indeed, several of the accepted analytic or empirical methods/models used to predict the behavior of metallic scaffolds tend to be unreliable, if not inappropriate, as methods/models for reliably and consistently predicting the highly non-linear, time dependent behavior of a polymeric load-bearing structure of a balloon-expandable scaffold. The models are not generally capable of providing an acceptable degree of certainty required for purposes of implanting the scaffold within a body, or predicting/anticipating the empirical data.

Polymer material considered for use as a polymeric scaffold, e.g. poly(L-lactide) ("PLLA"), poly(L-lactide-co-glycolide) ("PLGA"), poly(D-lactide-co-glycolide) or poly (L-lactide-co-D-lactide) ("PLLA-co-PDLA") with less than 10% D-lactide, and PLLD/PDLA stereo complex, may be described, through comparison with a metallic material used to form a stent, in some of the following ways. A suitable polymer has a low strength to volume ratio, which means more material is needed to provide an equivalent mechanical property to that of a metal. Therefore, struts must be made thicker and wider to have the required strength for a stent to support lumen walls at a desired radius. The scaffold made from such polymers also tends to be brittle or have limited fracture toughness. The anisotropic and rate-dependent inelastic properties (i.e., strength/stiffness of the material varies depending upon the rate at which the material is deformed, in addition to the temperature, degree of hydration, thermal history) inherent in the material, only compound this complexity in working with a polymer, particularly, bioresorbable polymer such as PLLA or PLGA.

Processing steps performed on, and design changes made to a metal stent that have not typically raised concerns for, or required careful attention to unanticipated changes in the average mechanical properties of the material, therefore, may not apply to a polymer scaffold due to the non-linear and sometimes unpredictable nature of the mechanical properties of the polymer under a similar loading condition. It is sometimes the case that one needs to undertake extensive validation before it even becomes possible to predict more generally whether a particular condition is due to one factor or another—e.g., was a defect the result of one or more steps of a fabrication process, or one or more steps in a process that takes place after scaffold fabrication, e.g., crimping. As a consequence, a change to a fabrication process, post-fabrication process or even relatively minor changes to a scaffold pattern design must, generally speaking, be investigated more thoroughly than if a metallic material were used instead of the polymer. It follows, therefore, that when choosing among different polymeric scaffold designs for improvement thereof, there are far less inferences, theories, or systematic methods of discovery available, as a tool for steering one clear of unproductive paths, and towards more productive paths for improvement, than when making changes in a metal stent.

The present inventors recognize, therefore, that whereas inferences previously accepted in the art for stent validation or feasibility when an isotropic and ductile metallic material was used, those inferences would be inappropriate for a polymeric scaffold. A change in a polymeric scaffold pattern may affect not only the stiffness or lumen coverage of the scaffold in its deployed state supporting a lumen, but also the propensity for fractures to develop when the scaffold is crimped or being deployed. This means that, in comparison to a metallic stent, there is generally no assumption that can be made as to whether a changed scaffold pattern may not produce an adverse outcome, or require a significant change in a processing step (e.g., tube forming, laser cutting, crimping, etc.). Simply put, the highly favorable, inherent properties of a metal (generally invariant stress/strain properties with respect to the rate of deformation or the direction of loading, little effect of body temperature or hydration, and the material's ductile nature), which simplify the stent fabrication process, allow for inferences to be more easily drawn between a changed stent pattern and/or a processing step and the ability for the stent to be reliably manufactured with the new pattern and without defects when implanted within a living being.

A change in the pattern of the struts and rings of a polymeric scaffold that is plastically deformed, both when crimped to, and when later deployed by a balloon, unfortunately, is not predictable to the same or similar degree as for a metal stent. Indeed, it is recognized that unexpected problems may arise in polymer scaffold fabrication steps as a result of a changed pattern that would not have necessitated any changes if the pattern was instead formed from a metal tube. In contrast to changes in a metallic stent pattern, a change in polymer scaffold pattern may necessitate other modifications in fabrication steps or post-fabrication processing, such as crimping and sterilization.

Scaffolds used to treat coronary vessels experience, for the most part, a primarily radial loading. However, scaffolds intended for peripheral vessels experience a quite different loading, to such an extent that the traditional measure of a stent's fitness for use, i.e., its radial strength/stiffness, is not an accurate measure of whether the scaffold will have sufficient strength to provide mechanical support within the peripheral vessel for the duration needed. This is because a peripheral scaffold is placed in a significantly different environment from a coronary scaffold. The vessel size is larger. And there is much more movement of the vessel, with motions in different directions, especially when located close to an articulating joint. As such, a scaffold intended for a peripheral vessel will need to be able to sustain more complex loading, including a combination of axial, bending, torsional and radial loading. See e.g. Bosiers, M. and Schwartz, L., *Development of Bioresorbable Scaffolds for the Superficial Femoral Artery*, SFA: CONTEMPORARY ENDOVASCULAR MANAGEMENT ('Interventions in the SFA" section). These and related challenges facing peripherally implanted stents and scaffolds are also discussed in U.S. application Ser. No. 13/015,474.

The art has previously addressed a need to reduce loading on ring elements due in-part to axial, bending, torsion or combination of these loads when the scaffold is implanted within a peripheral vessel. Previously proposed designs introduce frangible or significantly reduced stiffness in connecting links between ring elements, as in for example US 2011/0190972, or by forming a scaffold composed of several disconnected scaffold segments, as in U.S. application Ser. No. 13/840,257.

A continued need exists for addressing the loading environment of a peripherally-implanted scaffold, such as a scaffold implanted in the superficial femoral-artery including, but not limited to axial or longitudinally loading which can lead to fracture or weakening of struts forming ring elements; providing a coupling between scaffold segments while, at the same time, avoiding the creation of load paths into ring structures; and/or providing a coupling for maintaining a desired spacing between scaffold segments without losing any of the benefits of having a de-coupled or separate scaffold segments that in the aggregate form the scaffold for treating a diseased peripheral vessel.

SUMMARY OF THE INVENTION

According to one aspect a first and a second scaffold segment are connected only by a coupling as defined herein. In the absence of the coupling the first and second segments are not connected to each other.

The amount of movement experienced by a peripheral scaffold in the peripheral artery is greater than what a coronary scaffold experiences in the coronary artery. A peripheral scaffold can be subjected to a high degree of axial elongation/compression, pinching, bending (flexural), and torsion after implantation. The resultant stresses within the scaffold can be significant, especially with the longer scaffold (e.g., more than about 40 or 50 mm in length) used to support a peripheral vessel. The external forces applied by the peripheral-vessel's implant environment are believed to produce high stresses, in large part due to the presence of axial load paths between adjacent ring elements. The axial loads transmitted through these axial load paths can be a result of bending, torsion axial or a combination of these external loadings of the scaffold. Such forces or force resultants on ring elements are commonly often transmitted along the length of a scaffold link or horizontal/axial connecting element joining together adjacent ring elements. It is desirable to allow for a predetermined length of lost motion, or provide a lost motion distance (LMD) in response to an anticipated axial compression whereby for relative axial displacement within the span of the LMD no axial load is transmitted between adjacent rings. According to the invention, such structure providing this motion is provided by a coupling as defined herein.

In particular, for scaffolds greater than 40 or 50 mm in length non-radial or non-pulsatile loading can be significant; indeed, it can be a major factor in reduced fatigue life for a scaffold implanted within a peripheral vessel. One approach to addressing the reduced fatigue life is to decouple portions of the scaffold. That is, make a scaffold with segments placed adjacent each other, but not connected to each other in any way. While this approach can significantly reduce the loading on ring elements of the scaffold, it can also introduce several complexities relating to placement of all segments at the vessel location, as explained further herein.

In accordance with the invention a connection is formed between the segments that can significantly reduce a primary contributor to failure of scaffold structure; that is, axial loading. According to the embodiments a coupling is used to join segments in such a manner as to permit a finite range of relative axial displacement between the segments but without any transmission of axial loads through the coupling. By connecting scaffold segments in this way, segmented scaffolds may freely move over a limited axial distance relative to each other without transmitting axial loads. This limited axial distance, referred to herein as either a maximum distance between segments (Z1) and/or the lost motion distance (LMD), is defined by the type of coupling used.

According to one aspect of the invention, there is a scaffold, medical device, method for making such a scaffold, or method for assembly of a medical device comprising such a scaffold having one or more, or any combination of the following items (1)-(29):

(1) SEGMENTS. Segments are preferably made from a process where a tube comprised of a biodegradable polymer is radially or biaxially expanded above the TG of the polymer. A plurality of segments is cut from the radially expanded tube.

(2) A scaffold segment has a length or longitudinal extent at least equal to the segment's expanded diameter, pre-crimp diameter, as formed tube diameter or post-dilation diameter; the segments are composed of one or more cylindrical rings of struts; a cylindrical ring may be composed of undulating struts having crests and troughs. The cylindrical rings of struts of a segment are connected. The rings may be connected by link struts. Alternatively, the rings may be directly connected to one another without link struts. The number of rings in a segment may be one or any number greater than one. In some embodiments, a segment can have 1 or more, 2 or more, 1 to 6 rings, 1 to 3 rings, 2 to 6 rings, or 2 or 3 rings; the segments may have a network of struts forming diamond-shaped elements; and/or the ends, between which define the axial extent of the segment, may have undulations, sinusoidal, and/or zig-zag pattern about the circumference of the segment where the pattern has a Z-axis distance between peak to trough as defined by a Z-axis or axial length of a diamond or one half of this length.

(3) A segment joined by a coupling has a pattern as shown in any of FIGS. 8-12.

(4) SCAFFOLD: comprises at least two adjacent segments joined only by one, two, three or four couplings—nothing but one or more couplings joins the at least two segments; a scaffold comprises segments joined only by couplings, where between any or all adjacent segments there are one, two, three or four couplings joining the adjacent segments.

(5) The scaffold or segment is formed from a radially expanded tube having a diameter between 0.9 and 1.5 times the expanded or post-dilation diameter.

(6) Segments when connected by one or more couplings may or may not overlap each other. The degree of overlap can be about the axial length of a diamond-shaped element, or about ½ of this length, or the projection of about a strut length on the Z-axis.

(7) COUPLINGS. Scaffold segments are joined only by one or more coupling. A "coupling" is defined herein and this meaning is adopted throughout the disclosure and claims. A coupling has a LMD including a DOF in the Z-axis direction. When the adjacent segments are at a distance Z1 from each other they may only be moved towards each other without there being an axial load transmitted between the segments. In other words, when the scaffolds are at a distance Z1 from each other and an axial load tends to pull them farther apart, this axial (tensile) load is transmitted to rings of the segments via the coupling. When the segments are a distance Z2 from each other they may only be moved away from each other without there being an axial load transmitted between the segments. In other words, when the adjacent segments are a distance Z2 from each other and an axial load tends to push them closer together, this axial (compressive) load is transmitted to rings of the segments.

(8) A coupling is characterized by a maximum distance between segments (Z1), a minimum distance between segments (Z2) and a LMD in the Z-axis or axial direction whereby the LMD is the amount of free movement in the Z-axis direction permitted between segments before an axial load is transmitted between the segments, e.g., by surface-to-surface contact between the segments, via the structure of the coupling. As such, by allowing free movement axial load transmission to ring structure of a segment is reduced.

(9) A coupling may comprise one, two or three joints. A joint has at least a one degree of freedom (DOF) in the Z-axis, thereby permitting free or unstrained motion between segments over the LMD. The joint also may have one, two or three DOF in rotation.

(10) A first part of a coupling is formed, attached or secured at a peak or crown of segment A, and a second part of a coupling is formed, attached or secured at a peak or crown of segment B. The coupling extends between these peaks/crowns. Being that they are connected at crowns they do not interfere with radial expansion (balloon inflation) or contraction (crimping).

(11) A coupling does not add to, or affect the radial stiffness of a segment or joined segments.

(12) A portion of the coupling may be formed with a segment, or the coupling may be separate structure connected to the segment.

(13) There is an overlap of segments (i.e., same Z coordinate for rings of adjacent segments) connected by a coupling when the segments are a maximum axial distance (Z1) or only a minimum axial distance (Z2) from each other.

(14) Values LMD and Z1 for a coupling is any of the values or ranges, or any combination thereof of values and/or ranges as set forth in items a.-h. of section (viii) of the coupling definition, infra.

(15) METHOD OF MAKING. The steps including radially expanding a tube, forming a plurality of segments from the radially-expanded tube, and joining the segments with couplings.

(16) CRIMPING. Method for assembly includes crimping a scaffold comprising couplings and segments to a balloon include the step of disposing adjacent scaffolds at the distance Z1 prior to, or after a partial crimping of the scaffold to a balloon; or placing the scaffold in tension by pulling the ends away from each other so that the distance between adjacent segments is about Z1.

(17) Crimping also includes a pre-crimp or partial crimping step before fully crimping the segments to a balloon. The Z1 distance or Z2 distance between segments may be pre-set for a scaffold in relation to crimping. One or the other distance may be set prior to crimping, or after a partial crimping (e.g. after Stage II in FIG. 13A), to account for a shrinking or expansion of segments when crimped and/or deployed, so that the scaffold when implanted attains a desired Z or axial spacing between segments. Thus, the scaffold is compressed (Z2 distance set between segments) or placed in tension (Z1 distance set between segments) when being loaded on a balloon prior to crimping, or following a partial crimping (e.g. after Stage II in FIG. 13A).

(18) The medical device comprises a scaffold having segments and couplings, the scaffold is crimped to a balloon, the scaffold is encased in a sheath, and the medical device is configured for being implanted within a body only after the sheath is removed.

(19) A scaffold crimped to a balloon. The balloon nominal inflation diameter or expanded diameter is about 2.5, 3, 2-3, greater 2 times the size of the scaffold fully crimped diameter.

(20) A scaffold is made according to a method including forming a plurality of scaffold segments from a radially expanded tube. The segments made from the tube may include a portion of a coupling for connecting a first segment with a second segment. Alternatively, the coupling portion is separate from a segment that is connected by the coupling. That is, the coupling portion is not formed integrally with the segment, or made from the same tube.

(21) A segment A and segment B are connected by one or more of a thread, woven element, string, coupling or a combination thereof.

(22) Segments joined by a thread are joined by one or more threads that only extend between the outermost rings of adjacent segments, received only in slots or holes formed in the outermost rings, or tied to only the outermost rings.

(23) A thread, string or woven piece can be a continuous piece joining a plurality of peaks or crests of adjacent outermost rings of segments, or a plurality of threads, strings or woven pieces each joining a pair of adjacent crests or peaks of adjacent segments.

(24) There is a scaffold including a first segment comprising a polymer; a second segment comprising a polymer; and at least one coupling; wherein the first segment and the second segment are joined to each other by only the at least one coupling.

(25) The scaffold of (24), in combination with one of, or any combination of wherein the first and second segments are formed from a radially expanded tube; wherein the LMD and/or Z1 of the at least one coupling is at least about ½ the expanded or pre-crimp or as-formed diameter of the segment, the length of the Z-axis component of the strut, a strut length, and/or the distance between a peak and trough of a cylindrical ring formed by a plurality of struts; wherein the first or second segment have a pattern comprising struts and/or links arranged to form a closed space in the shape of a diamond, the diamond shape having an axial length; wherein the first or second segment has end rings forming end ring peaks and valleys, wherein an axial length between a peak and valley at the end ring is equal to ½ the axial length, the axial length of the diamond shape, or the length of two struts forming a portion of a diamond shape; wherein the LMD or maximum axial distance for the coupling is equal to either ½ the axial length or the axial length; wherein the coupling is one of a male-female coupling, a pin and socket coupling, or a flexible or stiff band coupling; wherein the coupling has a LMD or maximum axial distance that is about the length of a strut of the segment; about 0.3 to 0.5 times the expanded diameter of the first or second segment; about the axial distance between a peak and valley of an end ring of a segment; or about 7% to about 10% of the length of a scaffold segment; wherein the segments are joined by a beam, string or thread; and wherein when a thread or string, the string or thread joins together one pair of adjacent crests or peaks of the segments, or a plurality of pairs of adjacent crests or peaks; wherein the coupling comprises a first portion integral with the first segment, a second portion integral with the second segment, and a mechanical connection formed between the first and second portion; wherein the mechanical connection is one of a male and female connector, a flexible band, a stiff band, and a pin received in a slot; wherein a drug/polymer coating is disposed on surfaces of the scaffold; a maximum axial distance or Z1, or a lost motion distance LMD for the coupling, has any one of, or any combination of the values or ranges listed in Section (viii) of the coupling definition; wherein the at least one coupling does not increase a radial stiffness when joining the segments, does not prevent or restrain radial expansion of either segment and does not connect the segments in the axial direction over the LMD; and/or wherein each segment is formed form a radially expanded tube, and the at least one coupling has a first portion integral with the first segment, and a second portion integral with the second segment, wherein the first and/or second portions have a length defining an LMD or minimum axial distance of separation between the segments.

(26) According to another aspect, there is a medical device including the scaffold of item (24) or (25) crimped to a balloon; wherein the balloon has an expanded diameter; wherein the scaffold has a crimped diameter; and wherein the expanded diameter is at least 2, 3, or 3.5 times larger than the crimped diameter, or the balloon nominal inflation diameter is at least 2.5 times the crimped diameter. The scaffold may be arranged such that they are at a maximum or minimum axial distance permitted by the coupling.

(27) According to another aspect there is a method of making the scaffold of item (24) or (25) including manually joining the first segment to the second segment by engaging a first and second portion of the coupling and forming the segments from an expanded tube. The method may include either, or both of making the segments by at least one of laser cutting, injection molding, ion beam machining, patterning with a photoresist followed by etching; and providing a radially expanded tube and forming both segments and the at least coupling from the tube.

(28) According to another aspect there is a method of assembly including the steps configuring the scaffold of item (24) or (25) in a pre-crimping state including disposing the first segment and second segment at about a maximum or minimum axial distance permitted by the coupling; and crimping the scaffold to a balloon when the scaffold is configured in the pre-crimping state.

(29) The scaffold of (28), in combination with one of, or any combination of wherein the disposing step occurs before crimping, or after a partial crimping to an intermediate diameter, wherein the intermediate diameter is about a nominal inflation diameter of the balloon; wherein the crimping temperature is at about 5 to 15 degrees below Tg of the polymer of a segment; and/or wherein the scaffold has a pre-crimp diameter that is about equal to or greater than an expanded or post-dilation diameter for the scaffold; or about equal to a nominal or over-inflated diameter of the balloon.

INCORPORATION BY REFERENCE

All publications and patent applications mentioned in the present specification are herein incorporated by reference to the same extent as if each individual publication or patent application was specifically and individually indicated to be incorporated by reference. To the extent there are any inconsistent usages of words and/or phrases between an incorporated publication or patent and the present specification, these words and/or phrases will have a meaning that is consistent with the manner in which they are used in the present specification.

BRIEF DESCRIPTION OF THE DRAWINGS

FIGS. 1A-1B depict scaffold segments that are interconnected by couplings.

FIGS. 1C-1D depict a coupling illustrated as a slot, within which a first portion may freely move over a lost-motion distance (LMD) defined by the second portion.

FIG. 2 depicts a scaffold mounted on a balloon. The scaffold includes 3 segments connected to each other by two couplings. Unless otherwise noted, the rectangular coordinate system (X-Y-Z) in this figure is adopted everywhere in the description.

DETAILED DESCRIPTION

For purposes of this disclosure, the following terms and definitions apply:

The term "about" means 20%, 10%, 5%, 2% or 1% less or more than a stated value, a range or each endpoint of a stated range, or a one-sigma variation from a stated mean value.

"Inflated diameter" or "expanded diameter" refers to the diameter the scaffold attains when its supporting balloon is inflated to expand the scaffold from its crimped configuration to implant the scaffold within a vessel. The inflated diameter may refer to a post-dilation balloon diameter which is beyond the nominal balloon diameter, e.g., a 6.5 mm balloon has about a 7.4 mm post-dilation diameter, or a 6.0 mm balloon has about a 6.5 mm post-dilation diameter. The nominal to post dilation ratios for a balloon may range from 1.05 to 1.15 (i.e., a post-dilation diameter may be 5% to 15% greater than a nominal inflated balloon diameter). The scaffold diameter, after attaining an inflated diameter by balloon pressure, will to some degree decrease in diameter due to recoil effects related primarily to, any or all of, the manner in which the scaffold was fabricated and processed, the scaffold material and the scaffold design.

"Post-dilation diameter" (PDD) of a scaffold refers to the diameter of the scaffold after being increased to its expanded diameter and the balloon removed from the patient's vasculature. The PDD accounts for the effects of recoil. For example, an acute PDD refers to the scaffold diameter that accounts for an acute recoil in the scaffold.

Figure 3A:
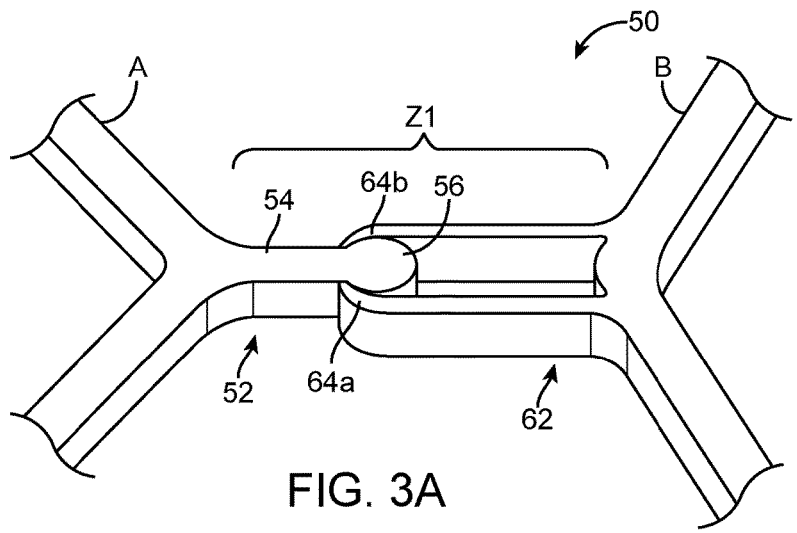
FIGS. 3A-3D illustrate a male-female structure joining segments according one aspect of the disclosure.
Figure 3B:
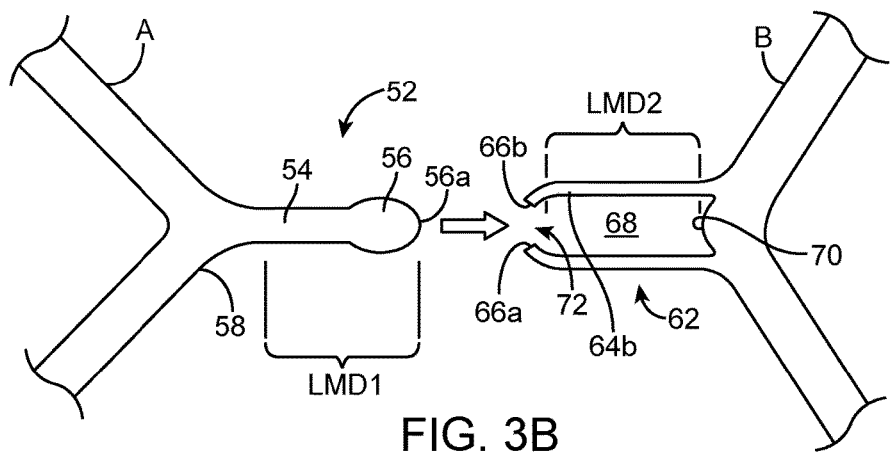

A "pre-crimp diameter" means an OD of a tube, or the scaffold before it is crimped to a balloon. Similarly, a "crimped diameter" means the OD of the scaffold when crimped to a balloon. The "pre-crimp diameter" can be 2, 2.5, 3.0 times greater than the crimped diameter and about 0.9, 1.0, 1.1, 1.3 and about 1-1.5 times higher than an expanded diameter or post-dilation diameter. A "partial crimp" diameter is a diameter attained after a scaffold or segment is crimped to a diameter less than a pre-crimp diameter and greater than a final crimp diameter. A partial crimp diameter can be an intermediate diameter after crimping from a pre-crimp diameter to about the nominal or over inflated diameter of the balloon to which the scaffold will be crimped. An example of a partial crimping diameter is described by the scaffold diameter following "Stage II" in FIGS. 3A and 4A, and described in U.S. application Ser. No. 13/644,347.

"Recoil" means the response of a material following the plastic/inelastic deformation of the material and in the absence of externally applied forces, e.g., vessel contraction. When the scaffold is radially deformed well beyond its elastic range and the external pressure (e.g., a balloon pressure on the luminal surface) is removed the scaffold diameter will tend to revert back to its earlier state before the external pressure was applied. Thus, when a scaffold is radially expanded by applied balloon pressure and the balloon removed, the scaffold will tend to return towards the smaller diameter it had, i.e., crimped diameter, before balloon pressure was applied. A scaffold that has recoil of 10% within ½ hour following implantation and an expanded diameter of 6 mm has an acute post-dilation diameter of 5.4 mm. The recoil effect for balloon-expanded scaffolds can occur over a long period of time. Post-implant inspection of scaffolds shows that recoil can increase over a period of about one week following implantation. Unless stated otherwise, when reference is made to "recoil" it is meant to mean recoil along a radial direction (as opposed to axial or along longitudinal direction) of the scaffold.

"Acute Recoil" is defined as the percentage decrease in scaffold diameter within the first about ½ hour following implantation within a vessel.

"Axial" and "longitudinal" are used interchangeably and refer to a direction, orientation, or line that is parallel or substantially parallel to the central axis of a stent or the central axis of a tubular construct. The term "circumferential" refers to the direction along a circumference of the stent or tubular construct. Thus, a link spaced 180 degrees from another link means 180 degrees as measured about the circumference of the tubular construct.

"Radial" refers to a direction, orientation, or line that is perpendicular or substantially perpendicular to the central axis of the stent or the central axis of a tubular construct and is sometimes used to describe a circumferential property, i.e. radial strength.

A "coupling" is a structure that connects or joins a scaffold segment A with a scaffold segment B so as to form a linkage having at least one joint. For example, shown in FIG. 2 are couplings 13a and 13b that connect scaffold segments 20, which are mounted on an inflated balloon 5. The structure of the coupling can be separate from both segment A and segment B then engaged with each segment to connect them. Or a portion of the structure is integral with one or each of segment A and segment B. Additionally, the structure when connecting the segment A and B must satisfy everyone of requirements (i)-(vii), infra, in order to be considered a "coupling" according to the invention (the following requirements may, or may not be mutually exclusive of each other):

(i) "Linkage" is defined at the Wikipedia web page under the sub folders "wiki" and "Linkage (mechanical)" downloaded May 7, 2013. Accordingly, a coupling has a joint defining degrees of freedom (DOF) for the joint. A ball-in-socket is a joint. A ball that linearly displaces and is confined within the length of a slot and can rotate within the slot, as depicted by the coupling in FIG. 1C-1D, is a linkage that has both rotational DOF and one translation DOF.

(ii) At least one joint is formed between the structure and each of, or only one of segment A and/or segment B, or by the structure itself.

(iii) The joint defines at least one degree of freedom (DOF) in translation along the Z-axis between the structure and each and/or one of the segments and up to three DOF in rotation. The joint may define motion in translation that may, or may not be parallel to the Z axis, e.g., a slot oriented at an angle to the Z axis.

(iv) When connected by the coupling, segment A may only move unrestrained towards segment B along the Z-axis only when the segments are a first or minimum distance (Z1) from each other, may only move unrestrained away from each other when segments are a second or minimum distance (Z2) from each other and may move unrestrained either away or towards each other when the segments are a third or intermediate distance (Z3) from each other, where Z1>Z3>Z2. Therefore, Z2 defines the minimum distance along the Z axis measured between segments A and B permitted by the structure; and Z1 is the maximum distance along the Z axis between segments A and B permitted by the structure (the term "permitted by" refers to the amount of motion that occurs before an axial load is transmitted between the segments, which can occur by either the coupling providing the axial load path during tension, a segment abutting a portion of the structure fixed to the other segment, or the segments abutting one another during compression, as examples). An example of Z1, Z2 and Z3 is shown in FIG. 1B.

(v) A coupling never locks adjacent segments together in the Z-axis direction, meaning a coupling, when joining segments, never prohibits all motion in the Z axis direction. Rather a coupling always provides free motion in the Z-axis direction; that is, relative motion between Segment A and B along the Z axis.

(vi) A coupling, when joining segments, does not increase the radial stiffness of either of the segments.

(vii) A coupling defines a lost motion distance (LMD) that is the amount of relative motion in Z or axially permitted between the segments, i.e., the LMD is equal to the difference Z1 and Z2. LMD is always less than or equal to z1. When the minimum distance between segments is defined by the abutment of the two segments (e.g., a crest of one segment coming into contact with a trough of the other segment, or opposed crests coming into contact with each other) then LMD=Z1 and Z2=0.

(viii) The Z1 and/or LMD distance can be any one, or a combination of a. through h.

a. Z1 and/or LMD is at least about the axial length from peak to trough of the outermost undulating ring, e.g., ring 322 in FIG. 7A; undulating end, e.g., axial length between peak 424 and trough 426 in FIG. 9; projection on the Z axis of a strut of a ring; ½ or entire length of a diamond-shaped element in FIGS. 8-9.

b. Z1 and/or LMD is always greater than about the length of a strut of a scaffold segment.

c. Z1 and/or LMD is always less than about the expanded or post-dilation diameter.

d. Z1 and/or LMD is at least about or about four times the distance between adjacent rings of one of the segments joined by the coupling.

e. Z1 and/or LMD is as large as possible but less than an amount that might lead to prolapse or focal restenosis of the vessel wall inward into the artery lumen at gaps between segments. Based on test data, prolapse was observed when the spacing was 5 mm. Z1 or LMD may be less than 5 mm.

f. Z1 and/or LMD is equal to, or greater than about 5%, 7% or 10%, or about 5-10% or 7-10% of the length of a segment, which is believed to correspond roughly to the maximum expected amount of enforced axial compression during normal walking. Thus, for example, a segment is 20 mm in length and a coupling provides a Z1 or LMD of 3 mm. If a scaffold, which includes the segment and coupling joining the segment to an adjacent segment, undergoes a 10% enforced compression then a ring of the segment should receive substantially reduced loads originating from adjacent segments because the enforced axial compression (i.e., 10%*23 mm=2.3 mm) is less than Z1 or LMD.

g. Z1 and/or LMD is about the length of a strut of the connected segment; about 0.25, 0.3 or 0.5, or about 0.25 to 0.5 times the expanded diameter of the segment; about the axial distance between a peak and valley of a ring of a segment such as the end ring or ring connected to the coupling; or about 5%, 7%, 10%, or about 5% or 7% to about 10% of the length of a scaffold segment. The later percentage is based on the estimate axial compression (as a percentage of overall scaffold length) that has occurred for a peripheral vessel implanted within the superficial femoral artery. Thus, for a coupling having an about 7-10% maximum axial length, Z1 or LMD, the axial loads resulting from an enforced compression of about 7-10% of the scaffold length will not transmit, or result in significantly reduced axial loads between connected scaffold segments.

h. Z1 and/or LMD is chosen based on the amount of bending of the scaffold. Bending of a vessel with implanted segments results in a decrease in the Z axis distance, i.e., segment A moves closer to segment B, at the concave or inner side of the bend with the gap widening toward the convex or outer side of the bend. The segments at the inner side of the bend may interfere or make contact with each other (notwithstanding the presence of the coupling defining a Z2 distance) if the initial gap is not wide enough. Therefore the Z1 or LMD distance can be chosen for the coupling to allow for bending of up to 10, 20 to 30 degrees or less than 30 degrees, or about 30 degrees of one scaffold relative to the adjacent scaffold joined by a coupling. Z1 or LMD for the coupling may be about $\frac{1}{2}*D*\tan(\varphi)$ where D is a pre-crimp, as formed tube, expanded or post-dilation diameter and $\varphi$ is 10, 20, 10 to 30 degrees or less than 30 degrees, or about 30 degrees ($\varphi$ is rotation of a segment 20 within the plane of the paper in FIG. 2, i.e., about the r axis). For example, for a 6 mm post-dilation diameter Z1 and/or LMD may be between about 0.53, 1.1 and 1.7 mm or about 10%, 20% or 30% of the post-dilation diameter.

A "maximum axial distance" means Z1, or the maximum amount of separation between the segment A and segment B when joined by one or more couplings. In some embodiments LMD=Z1. Every coupling has an inherent maximum axial distance when the coupling is joining the two segments.

FIGS. 1A-1D show, schematically, scaffold segments 10a-10d connected to each other by couplings 13a-13c for purposes of further explanation of the properties of a coupling according to the disclosure. Referring to FIGS. 1A, 1B a coupling 13a consisting of two parts—male portion 11a and female portion 12a—may have the male portion 11a formed integral with segment 10a and the female portion 12a formed integrally with segment 10b, or they may both be separate from segments 11a and 11b and fixed thereto, respectively. When the male portions 11a-c are engaged with their respective female portions 12a-c (as shown in FIG. 1B) the resulting couplings 13a, 13b, 13c each permit relative motion between adjacent segments in only the Z translational direction (assuming the coupling 13a permits segment 10a to rotate about the Y axis relative to segment 10b, this rotation will allow segment 10a to translate in X relative to segment 10b, but in the absence of the Y axis rotation no relative motion in X is permitted by the coupling 13a). When the segments joined by the coupling are disposed at the maximum distance (Z1) from each other permitted by the coupling, the coupling 13a, b only permits motion in Z that brings the segments closer together. When the distance is Z3 the segments may move apart in Z or closer together. When the distance is Z2 the segments may only be moved farther apart. The difference between Z1 and Z2 is the LMD for the coupling 13. FIG. 1C and FIG. 1D illustrate further the concept of the LMD. For the illustrated pin within the axially extending slot the LMD is the amount of distance in Z the pin can freely move back and forth within the slot. The LMD is equal to the axial space within which the pin can move axially back and forth within the slot.

Following are examples of structure forming a coupling that connects a segment A and B. With regard to the segment A and B connected by the coupling, the structure of the segments can be the same or different between A and B. Preferred embodiments of segments according to the disclosure are found in FIGS. 7-12 and U.S. application Ser. No. 13/584,678. An example of a scaffold 780 comprised of seven segments 782, each having diamond-shaped elements 784, where each segment is joined to an adjacent segment by two couplings 13 spaced about 180 Degree apart, is illustrated in FIG. 12.

In the examples of FIGS. 3-6 the coupling is shown being formed on or near, or connected on or near a crown or peak of a scaffold segment A and B. However, for any of these embodiments the coupling can be formed on or near, or connected on or near a trough, or valley; segment A may have its coupling portion formed on or near, or connected on or near a trough or valley while the segment B may have its coupling portion formed on or near, or connected on or near a crown or peak.

It will be understood that various combinations of structural or functional features of the embodiments of couplings, including those embodiments illustrated in the examples of FIGS. 3-6, can be combined with one another. Accordingly, in some embodiments of the invention examples of couplings according to the disclosure are not mutually exclusive of each other.

According to any of the embodiments, the segment A may be connected via one coupling or via two couplings 50 spaced 180 degrees apart from each other, three couplings spaced 120 degrees apart or four couplings spaced 90 degrees apart.

According to some embodiments, the segment A and segment B are connected only by a coupling. Thus, for any of the disclosed methods of assembly, or assembled scaffolds, only couplings connect adjacent segments, or couplings are the only in-plane connecting structure between adjacent segments. In other embodiments, additional structure may connect the adjacent segments.

FIGS. 3A-3D depict aspects of a first embodiment of a coupling, which may be regarded as a ball and socket type coupling according to the disclosure. The coupling 50 includes a pin or male portion 52 and a slot female portion 62. The male and female portions 52, 62 are formed integrally with the respective segments A and B, as illustrated. Additionally, a rivet, pin or cover, illustrated schematically as top and bottom covers, pieces or heads 80, 82 welded or glued to the inner and outer surfaces of the female portion 62 to retain the male portion within the female slot 68 during movement of the segment A or B. As such, there is only Z translation permitted between segment A and segment B. Specifically, when the segments A and B are spaced by Z1, FIG. 3A, they may only freely translate towards each other. And when the segments A and B are spaced by Z2, FIG. 3D, they may only freely translate away from each other.

The DOF of the joint defined by coupling 50 is Z translation only.

The Z1 distance for coupling 50 is created when the head 56 of the male portion 52 is proximal the opening 72 into the female space 68 and distal an abutting surface 70 offset in the Z-axis direction from the opening 70; or when the head 56 is spaced by about the LMD from the surface 70.

Figures 3C, 3D:
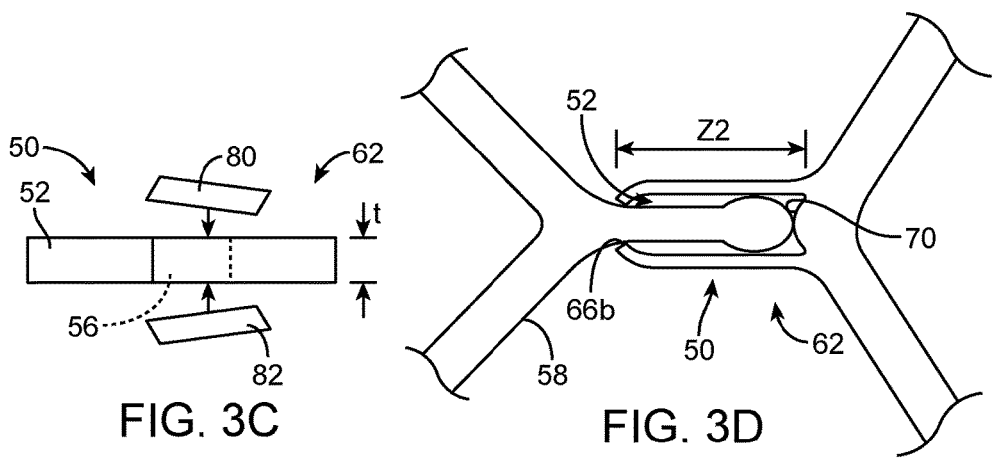

The Z2 distance for coupling 50 occurs when the surface 56a of head 56 of male portion 52 abuts surface 70 of female portion 62 or in this example crown surface 70 of segment B, and/or edges 66a, b of arms 64 of female portion 62 come into contact or abut a surface 58 of segment A, as illustrated. The LMD for coupling 50 may be defined in two alternate ways. The LMD may be LMD1, in which case the LMD is defined by the length of the male portion 52. And/or the LMD may be LMD2, in which case the LMD is defined by about the length of the female portion upper and/or lower arms 64. The illustration of FIG. 3D shows the case where LMD1=LMD2. As can be appreciated from FIG. 3A or 3B the male and female portions 52/62 can have unequal lengths.

In a method of assembly, the segment A and B are connected by forcible pressing the male head 56 into the female space 68. To facilitate this assembly, a chamfered surface may be formed at the edges 66, which are sized to flex outwardly when the rounded male head 56 is forcibly pressed against surfaces of the edges 66. Once pressed into the space 68 the shapes of the edges 66 of arms 64 prevent or discourage dislodgement of the male portion 52 from the female portion 62.

Referring to FIG. 3C, the coupling 50 may be substantially formed from the tube from which the scaffold segments are formed. The tube has a thickness t, as shown in FIG. 3C. After assembly of the segment A to B via the coupling 50 the rivet, or cover is welded or glued to the head 56 so as to retain the male portion 56 within the space 68.

Figure 4A:
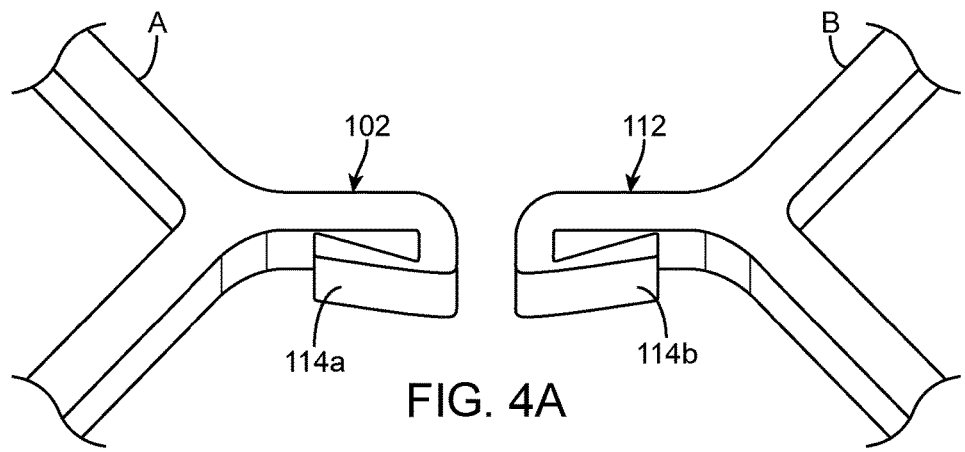
FIGS. 4A-4D illustrate a flexible structure joining segments according another aspect of the disclosure.
Figure 4B:
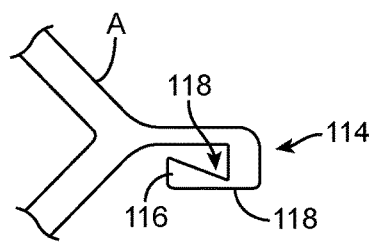
Figure 4C:
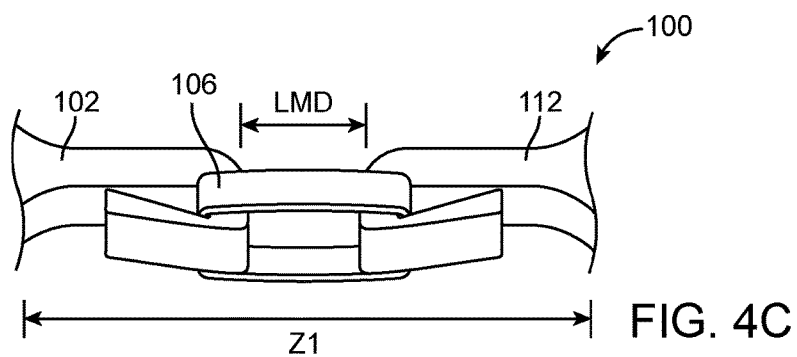
Figure 4D:
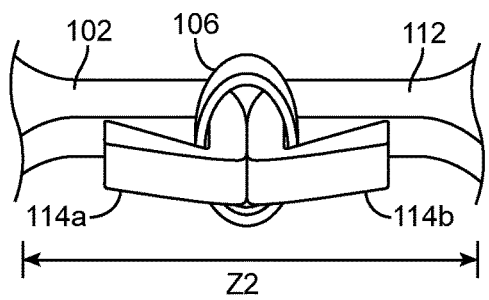

FIGS. 4A-4D depict aspects of a second embodiment of a coupling, which may be regarded as a flexible coupling or hook and loop coupling according to the disclosure. The coupling 100 includes identical arms 102, 112 forming hooks 114a and 114b configured to receive a flexible band 106. FIGS. 4C and 4D show the fully assembled coupling 100. FIG. 4A shows the coupling 100 less the flexible band 106. Referring to FIG. 4B the hook 114 may include an edge 116 configured to deflect outwardly about a living hinge 118 formed as a narrowed portion of the material, as illustrated. The flexible band 106 may then be slipped into the space 118 where it is retained. The flexible band 106 may be made of a bioresorbable elastomer, e.g., a "rubber band" or a flexible bioresorbable polymer. The segment is made from a first polymer and the band is made from a second polymer, wherein the second polymer has a material stiffness that is substantially less than (i.e., by a factor of 2, 5, 10) and/or elongation to break that is substantially greater (i.e., by a factor of about 2, 3, 8) than the first polymer. The arms 112 and 102 are formed integrally with the respective segments A and B, as illustrated.

The DOF of the joint defined by coupling 100 is Z translation only and rotation about the one of the X or Y axes in two places, i.e., where the flexible band 106 is engaged about the left and right pieces 114 as shown in FIG. 4C. It is understood that since the flexible band is made from an elastomer, a relatively small amount of force in X or Y will result in relative movement between arms 112 and 102 in these translation directions. However, for purposes of this disclosure the linkage has only one DOF in translation, which is translation in the Z-axis direction.

When the segments A and B are spaced by Z1, FIG. 4C, they may only freely translate towards each other. And when the segments A and B are spaced by Z2, FIG. 4D, they may only freely translate away from each other.

The Z1 distance for coupling 100 is created when the flexible band 106 comes into tension, or when a restoring force in the flexible band becomes non-zero if the segments A and B are pulled farther apart.

The Z2 distance for coupling 100 occurs when the ends 114a and 114b abut one another, as shown in FIG. 4D.

The LMD for coupling 100 is the maximum space formed between the ends 114a, 114b before the flexible band 106 begins to impart a restoring force tending to resist the segments A and B being pulled away from each other.

The arms 102 and 112 of coupling 100 may be formed from the tube from which the scaffold segments are formed.

Additionally, coupling 100, like coupling 50 has Z1 not equal to about the LMD. In the case of couplings 50 and 100 the LMD is less than Z1, as can be appreciated by the fact that Z2 is non-zero. In the case of coupling 50 the Z2 is equal to about the shorter-in-length (in Z axis direction) of the male portion 52 and female portion 62. In the case of the coupling 100 the Z2 length is about equal to 2× the length of an arm 102/112.

Figure 5A:
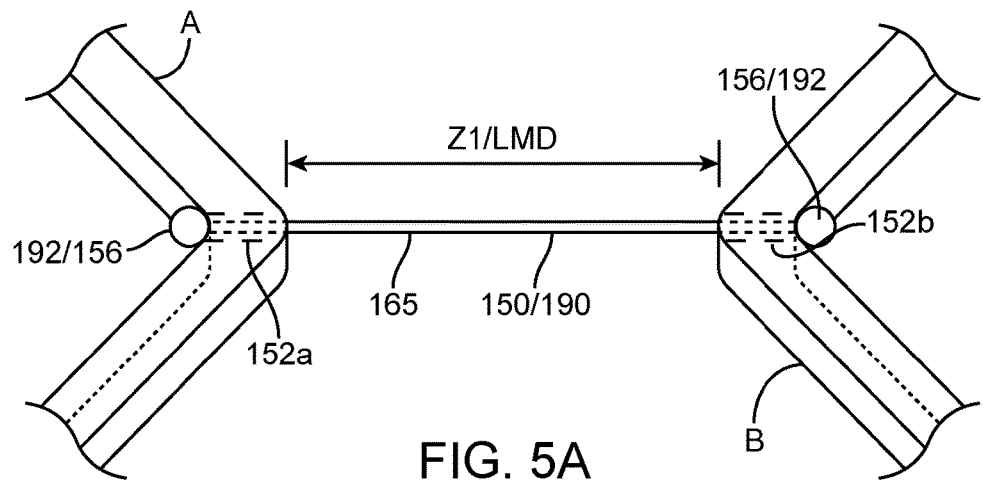
FIGS. 5A-5F illustrate a beam, string or thread joining segments according another aspect of the disclosure.
Figure 5B:
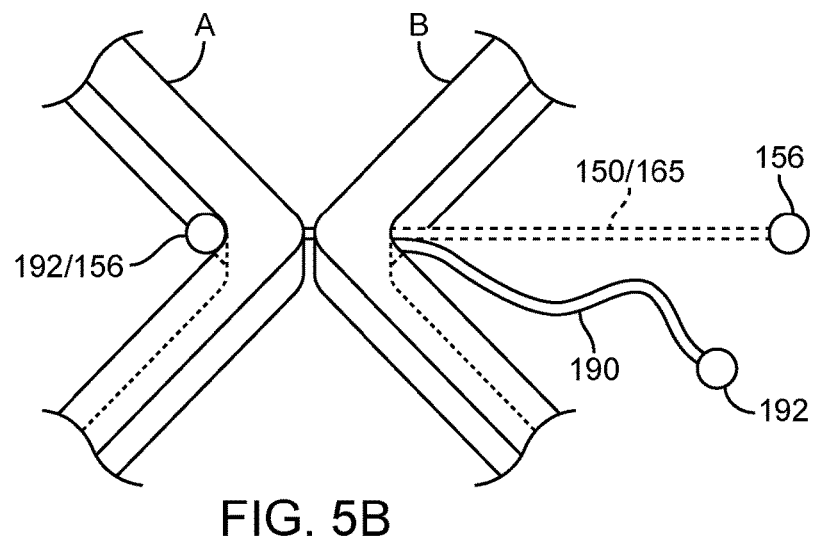

FIG. 5A illustrates a coupling 150 that is in the form of a beam 165 (i.e., a body that has bending stiffness) received in bored holes 152a/152b in segments A and B. The beam, which may be formed from the same polymer as the tube, has enlarged ends to prevent the ends 156 of the beam from escaping from the holes in which it is retained to the segments. The ends 156 may be formed by melting/flattening ends of a larger beam to enlarge the cross-sectional sizes.

The DOF of the joint defined by coupling 150 is Z translation only and rotation about only the Z axis in two places, i.e., where the ends of the beam 165 are received in the holes 152a, 152b. Z axis rotation is available when the beam 150 has a round cross-section and is received in a round hole.

When the segments A and B are spaced by Z1, FIG. 5A, they may only freely translate towards each other. And when the segments A and B are abutting each other, FIG. 5B, they may only freely translate away from each other.

The Z1 distance for coupling 150 is created when the segments A and B are pulled apart until the ends 156 of the beam 165 both reach the respective holes 152a, 152b, or about when the beam 150 is brought into tension. The Z2 distance is zero, as can be appreciated from FIG. 5B. Thus, in this example LMD=Z1.

Alternatively, a connection may be made between the segments A and B by a thread or string 190 made from a bioresorbable material. The string or thread by its nature cannot sustain a bending load or transverse. As such, in the configuration of FIG. 5A-5B when not in tension the string 190 permits translation in X and Y, in addition to Z. The string has ends 192 to keep it within the hole.

In a method of making the scaffold segments configured for receiving either the beam 165 or the string 190 a hole may be bored out of the tube by a laser, or a wire embedded then later removed to form the passageway for the string 190 or beam 165. Then the segments may be cut from the tube using a laser and the segments connected to each other by the thread 190 and/or beam 165.

Figure 5C:
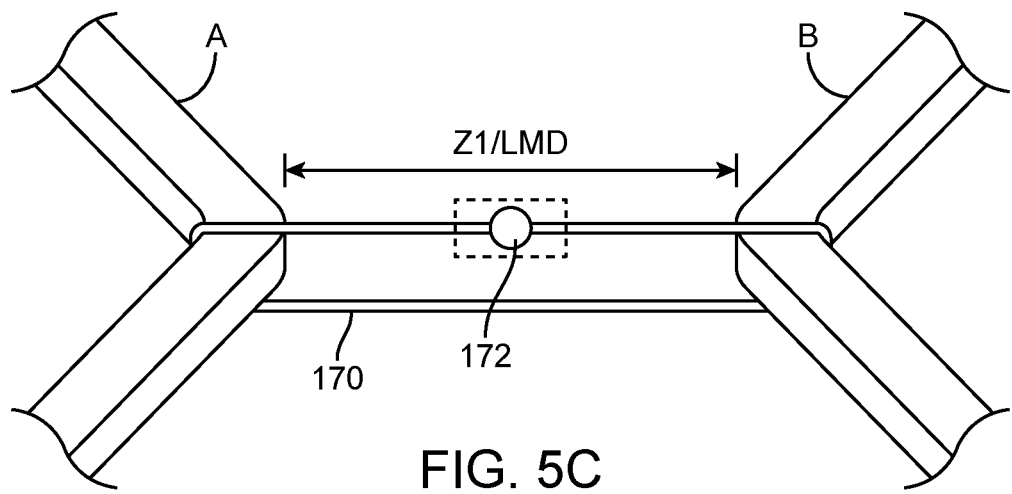
Figure 5D:
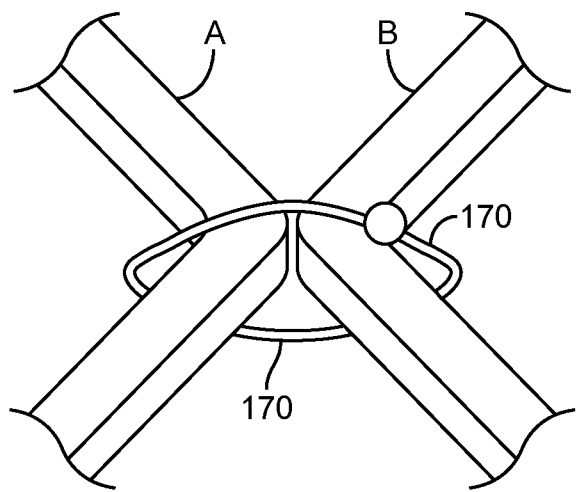

Another embodiment of a string connecting segments A and B is shown in FIGS. 5C-5D. The thread or string 170 is wrapped around ends of the segment A and B and then tied together at 172. This embodiment has the advantage that a hole need not be made in the struts of the segments, which may be preferred both form the perspective of not weakening rings of the scaffold segments by boring a hole in the segments, as well as simplification of the manufacturing processing for the segments.

The LMD is equal to Z1 in the case of a string or thread 170 or 190.

Referring again to FIG. 5C, in yet another embodiment the structure 170 may be a relatively stiff band, or flexible band 170 made from an elastomer wrapped around the opposing (or nearby) respective peaks or valleys of end rings of adjacent Segments A and B. A flexible band (made from an elastomer) or stiff band (made from the same material as the segment and shaped as a band with overlapping ends) may be used as a coupling connecting the segments by first wrapping the band around the respective end rings then tying the ends together in a similar manner as indicated by tie point 172 in FIG. 5C. The LMD is equal to Z1 in the case of a flexible or stiff band 170. And Z1 is obtained when the band is first brought into tension as the segments A and B are pulled away from each other. The band 170 will shift, slide or move towards and then nestle or arrive at the crowns when the segments are pulled away from each other, to thereby form the Z1 length.

Figure 5E:
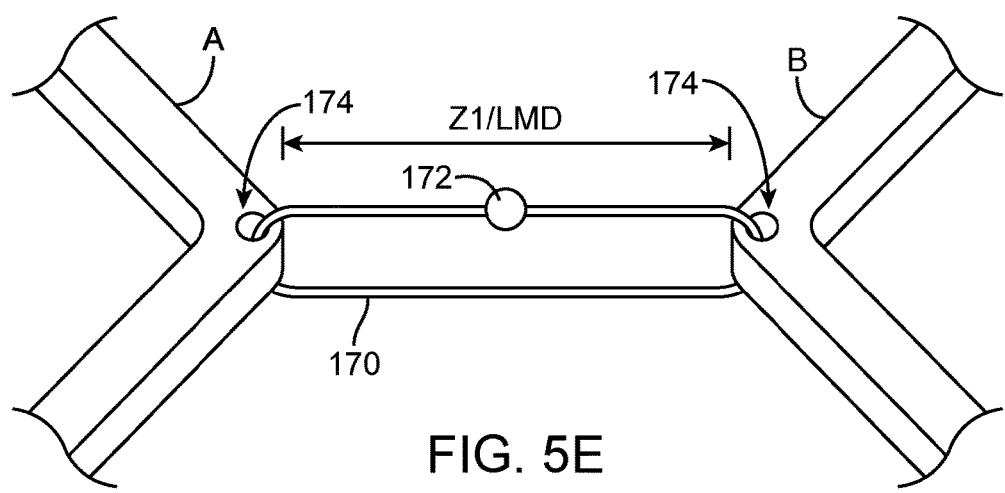
Figure 5F:
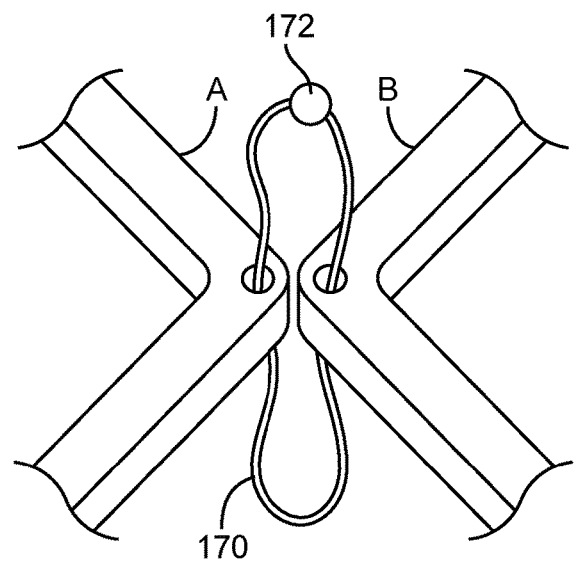

FIGS. 5E-5F show a modification of the coupling 170. In this embodiment the coupling 170 is received in holes 174 formed at or near the crests of the segments A and B. Other than this change, the same features apply to this embodiment of a coupling as described above in connection with FIGS. 5C-5D.

Figure 5G:
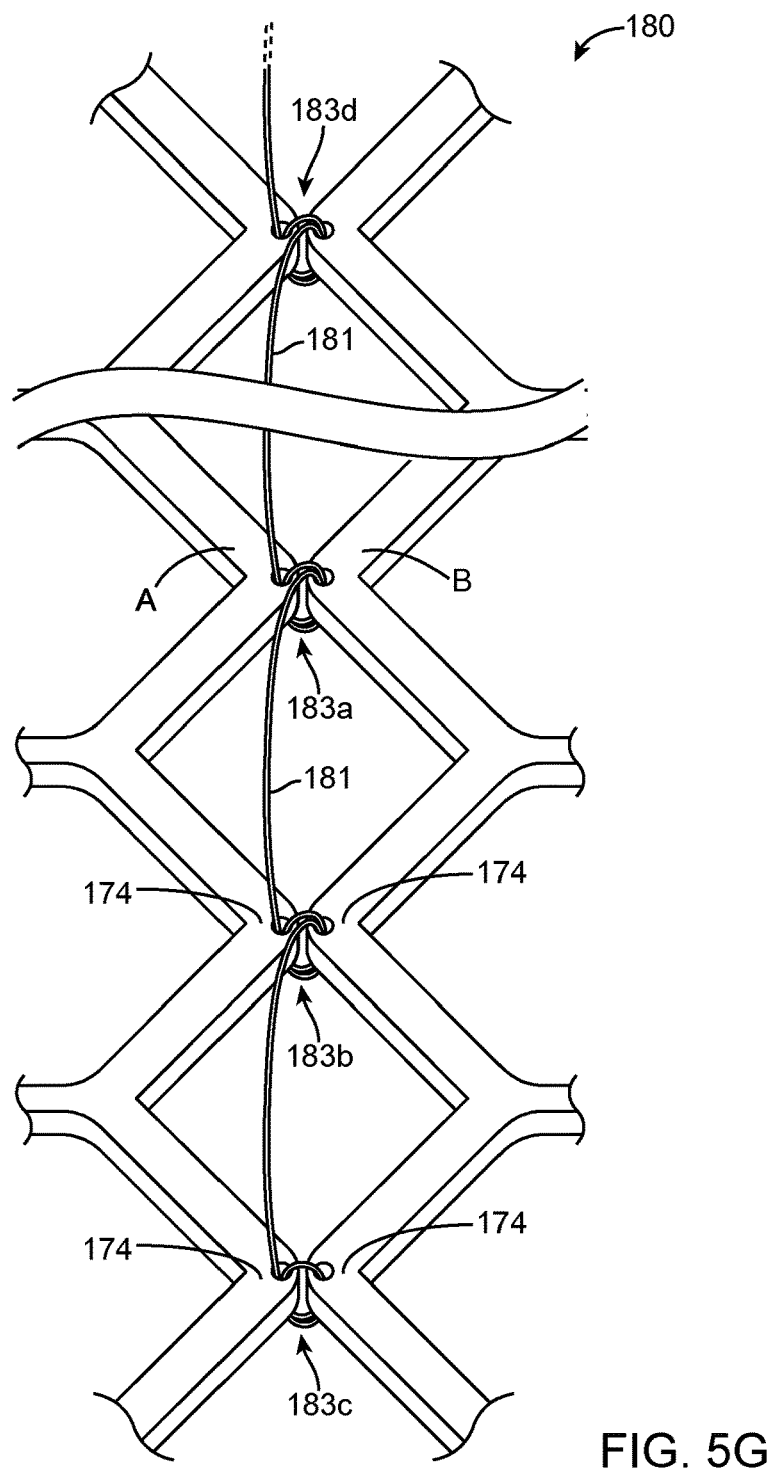
FIGS. 5G-5H illustrate a continuous threading joining segments according another aspect of the disclosure.
Figure 5H:
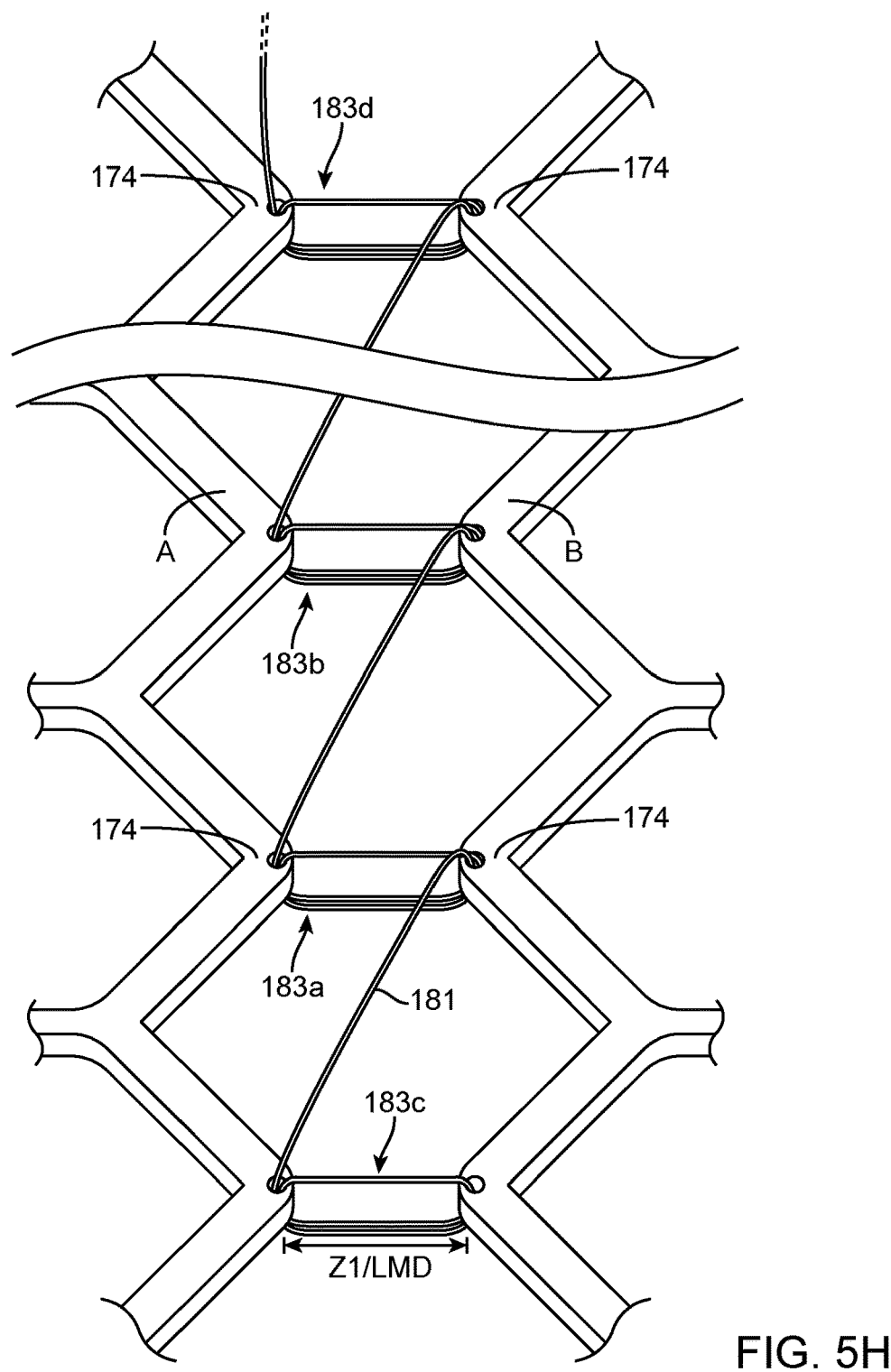

FIGS. 5G-5H show an embodiment of a coupling 180 where a continuous piece of threading 181 joins a segment A and B at plurality of crest or peak locations at an edge of the segments. The threading 181 is received in holes 174 and threading across peaks to form coupled regions 183a, 183b, 183c and 183d as shown. At each coupled region there is a Z1 that is the same as the LMD, and Z2=0. The coupling 180 may join each opposing peak, every other peak, or may join peaks located 180, 120 or 90 degrees apart (i.e., the threading is done in such a manner that there are 2, 3, or 4 regions 183 spaced evenly apart from each other).

FIGS. 6A-6D depict aspects of another embodiment of a coupling 200, which may be regarded as a pin and slot coupling according to the disclosure. The coupling 200 includes a pin portion 202 and a pair of slot portions 204a and 204b formed in struts of segments A and B. Flattened ends 206 are made on the pin 202 after it is placed within the slots 204 to retain the pin 202 within the slots 204.

The DOF of the joint defined by coupling 200 is translational motion in both Z and Y and rotation about Y, or Z and X and rotation about X. There is such a joint between Segment A and pin 202 and segment B and pin 202. When the segments A and B are spaced by Z1, FIG. 6C, they may only freely translate towards each other. And when the segments A and B are spaced by Z2, FIG. 6D, they may only freely translate away from each other.

Figure 6A:
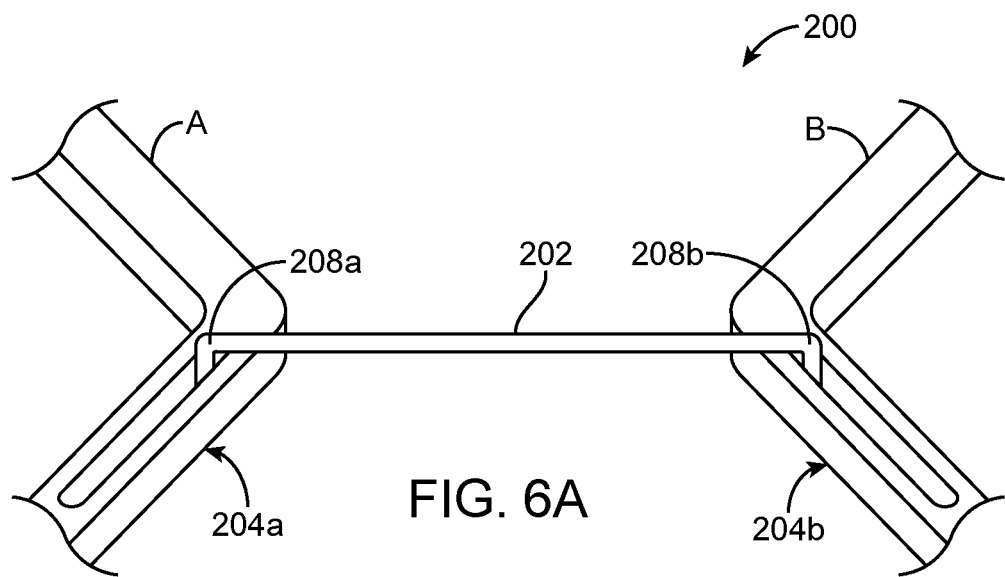
FIGS. 6A-6D illustrate a pin and slot structure joining segments according another aspect of the disclosure.
Figure 6B:
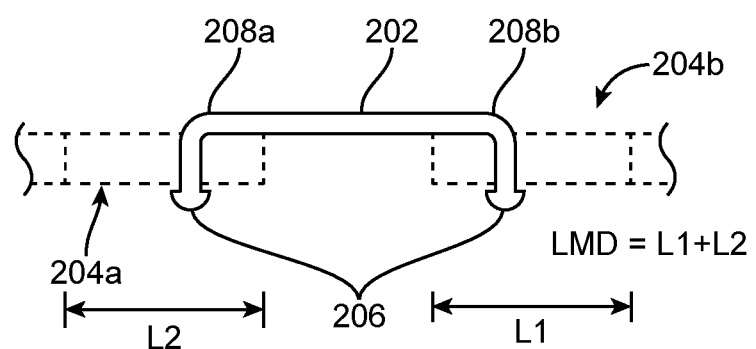
Figure 6C:
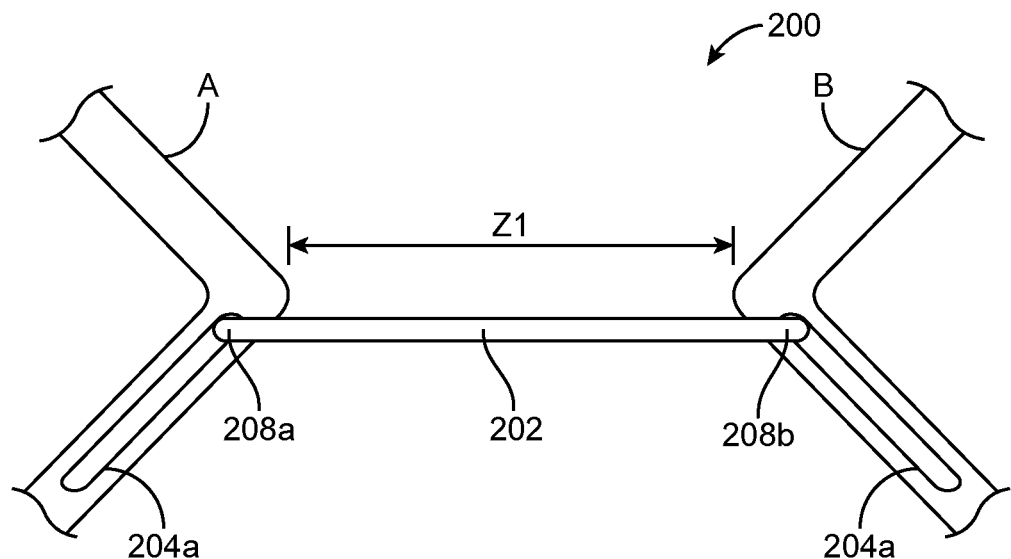

Referring to FIG. 6C, The Z1 distance for coupling 200 is created when both ends 208a, 208b are closest to the respective crowns or peaks of the segments A and B, or proximal the crown and distal the trough or valley of the undulating or zig-zag end ring of the segments A and B.

Figure 6D:
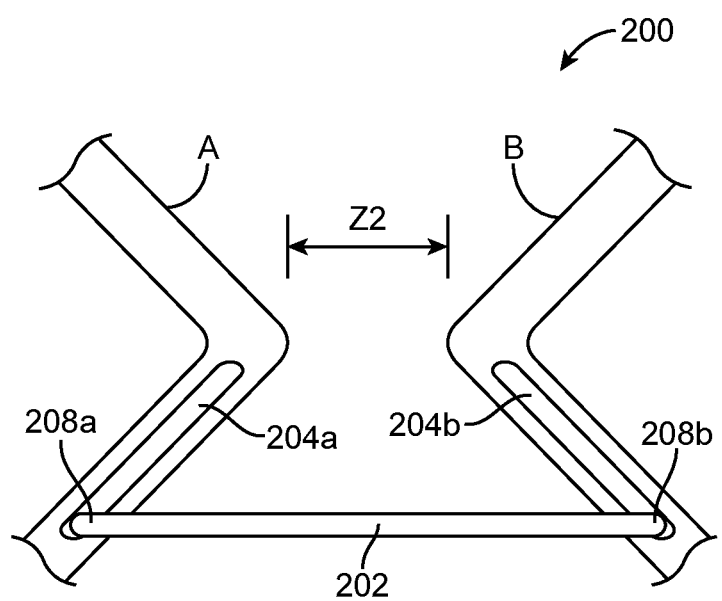

Referring to FIG. 6D, the Z2 distance for coupling 200 occurs when both ends 208a, 208b are closest to the respective trough or valley of the segments A and B, or proximal the trough or valley and distal the peak or crown of the undulating or zig-zag end ring of the segments A and B.

The LMD is illustrated in FIG. 6B, which shows the projection of the slot 204a, 204b length onto the Z axis. The magnitude of the LMD for this embodiment is the sum L1+L2.

Segments

A segment according to the invention may include a portion of one, two, or three couplings at one or both ends. For example, a segment connected by a coupling formed, at least in part, with the segment, i.e., integral with the segment, such as the example in FIG. 3A-3D, has one, two or three of a first part of the coupling formed at one end and one two, or three of a second part of the coupling formed at the opposite end for connecting the segment to adjacent left and right segments, as depicted in FIG. 2.

Figure 7A:
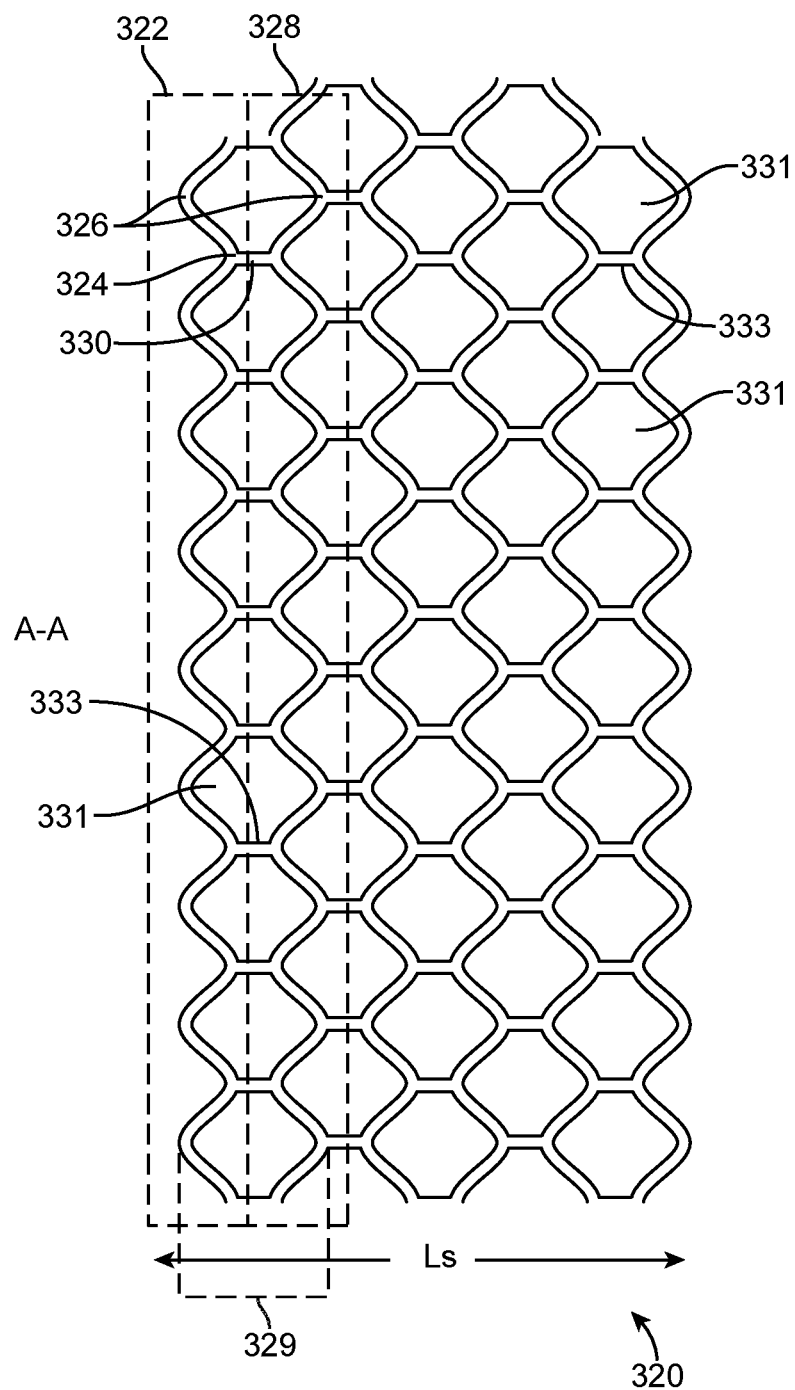
FIG. 7A illustrates a first pattern for a segment according to another aspect of the disclosure.

FIG. 7A depicts an exemplary axial scaffold segment 320 viewed in a flattened configuration composed of a plurality of rings of undulating struts with crests and troughs. Line A-A is the longitudinal or Z axis of the segment. An exemplary ring 322 has crests 324 and troughs 326. As shown in FIG. 7A, every crest in ring 322 is connected to every trough in adjacent ring 328 by a short link strut 330. The arrangement of rings 322 and rings 328 forms a plurality of rings 329 of diamond-shaped elements 331 formed of struts. The diamond-shaped elements 331 of the rings are connected at circumferentially aligned vertices of the diamond-shaped elements.

Ls is the length of the segment 320. Ls may be 3 to 6 mm, 6 to 8 mm, 8 to 10 mm, 10 to 12 mm, or greater than 12 mm in an as cut or as fabricated configuration. For this type of segment, Ls increases when the segment is crimped to a decreased diameter and then decreases when expanded from a crimped configuration. Length change is affected by the number of peaks in a ring and the width of the diamonds. The length change (increases or decreases) with the number of peaks and (increases or decreases) with the width of the diamonds.

Figure 7B:
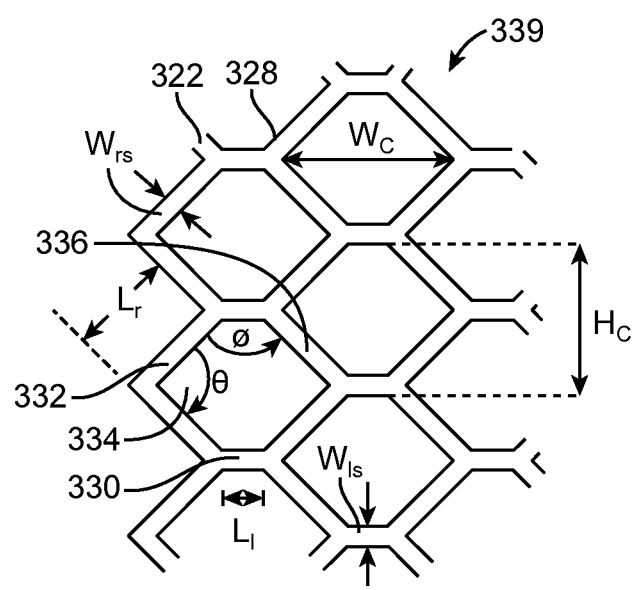
FIG. 7B is a close-up view showing a portion of the segment of FIG. 7A.

FIG. 7B depicts a close-up view of a portion 339 of axial segment 320 illustrating various features. As shown in FIG. 7B, Lr is the length of a ring strut, for example, strut 332 between a crest and trough in a ring and Wrs is the width of the ring strut. $L_l$ is the length of short link strut 330 that connects crests and troughs of adjacent rings and Wls is the width of the link strut. θ is the angle at the longitudinal vertex of the diamond shaped cells, i.e., between struts 332 and 334 in a ring that intersects at a crest or trough. Ø is the angle between struts 332 and 336 which are joined by short link strut 330 and a diamond-shaped cell. Hc is the height of the diamond-shaped cell and Wc is the width of the diamond-shaped cell.

θ may be 90 degrees, 90 to 95 degrees, 95 to 100 degrees, 100 to 110 degrees, or greater than 110 degrees. θ may be 90 degrees, 85 to 90 degrees, 80 to 85 degrees, 70 to 80 degrees, or less than 70 degrees. Ø may be 90 degrees, 85 to 90 degrees, 80 to 85 degrees, 70 to 80 degrees, or less than 70 degrees. Ø may be 90 degrees, 90 to 95 degrees, 95 to 100 degrees, 100 to 110 degrees, or greater than 110 degrees.

Exemplary values for θ and Ø are about 70 and 110 degrees, respectively. Values in this range tend to reduce segment shortening from crimping to deployment. Other exemplary values for θ and Ø are about 110 and 70 degrees, respectively. Values in this range tend to increase segment's radial strength and crush resistance. Another variable that affects the angles above is the lased tube diameter and the final deployed diameter. Generally, for polymers, the lased tube diameter is slightly larger than the final deployed diameter.

The segments can include radiopaque marker embedded within holes in the scaffold segment to aid in visualization of the implanted scaffold. In some embodiments, the markers are embedded in holes in the short link struts 330 of FIG. 7A. In other embodiments, the markers are embedded in holes in ring struts 332 of FIG. 7B.

Referring to FIG. 7A, when a scaffold segment is crimped, the Ls increases, which is caused by bending at the vertices of the diamond-shaped elements. Specifically, when the scaffold segment is crimped, θ decreases and Ø increases. When a scaffold segment is deployed, the Ls shortens which is caused by bending at the vertices of the diamond-shaped elements corresponding to an increase in θ and a decrease in Ø.

The segment properties of radial strength and stiffness can be modified through adjustment of the as-cut geometrical parameters of the diamond-shaped elements. For example, radial strength and stiffness is increased by increasing Hc which results in a decrease in Wc and also corresponds to a decrease in Ø and an increase in θ.

In some segment design embodiments, the diamond-shaped elements are square-shape or approximately square-shaped in the as-cut condition. In such embodiments, Ø is the same or approximately the same as θ. For example, ABS(Ø−θ) may be 2 or about 2 degrees or less than 2 degrees.

In other segment design embodiments, the diamond-shaped elements can be taller or greater in the circumferential direction or, Hc>Wc and Ø>θ. In such embodiments, the θ−Ø may be greater than 2 degrees, 2 to 4 degrees, 4 to 8 degrees, greater than 8, about 3 degrees, about 4 degrees, or about 5 degrees.

$L_l$ may be less than 10% or 10% to 20%, 20% to 30%, 30 to 40%, or greater than 40% of a ring strut length between a crest and a trough. Exemplary link struts may have a length of less than 0.01 in, 0.01 to 0.02 in, 0.02 to 0.04 in, 0.04 to 0.06 in, or greater than 0.06 in. In some embodiments, adjacent rings are connected at an intersection of the opposing crests and troughs such that a length of the link strut is effectively the width of the intersection and $L_l$ is zero.

As discussed in U.S. application Ser. No. 13/584,678 a scaffold including a plurality of unconnected segments presents challenges with regard to crimping on a delivery balloon including maintaining the desired spacing between segments, placing segments and ensuring no overlapping of segments.

Generally, scaffold crimping is the act of affixing a radially expandable scaffold or stent to a delivery catheter or delivery balloon so that it remains affixed to the catheter or delivery balloon until the physician desires to deliver the stent at the treatment site. Examples of crimping methods are described. According to one aspect of the invention crimping of a scaffold according to the disclosure includes one or more of the crimping steps set forth in FIGS. 13A and 13B (balloon A is the balloon of the catheter and balloon B is a sacrificial balloon that may be used during the crimping to an intermediate diameter). The crimping may including a crimping temperature of about 5-15 degrees below the glass transition temperature of the polymer used to form the tube.

Examples of crimping technology include a roll crimper; a collet crimper; and an iris or sliding-wedge crimper. In the sliding wedge or iris crimper, for example, adjacent pie-piece-shaped sections move inward and twist toward a scaffold in a cavity formed by the sections, much like the leaves in a camera aperture.

The Z1 distance or Z2 distance between segments may be pre-set for a scaffold in relation to crimping. One or the other distance may be set prior to crimping, or after a partial crimping (e.g. after Stage II in FIG. 13A), to account for an axial shrinking or axial expansion of segments when crimped and/or deployed, or to account for movement when the balloon is expanded, so that the scaffold when implanted attains a desired Z or axial spacing between segments. Thus, according to embodiments of crimping, the scaffold is compressed (Z2 distance set between segments) or placed in tension (Z1 distance set between segments) when being loaded on a balloon prior to crimping, or following a partial crimping (e.g. after Stage II in FIG. 13A).

A scaffold segment having rings forming zig-zag patterns interconnected by links tend to not shorten or lengthen during crimping and deployment. Scaffold segments having diamond-shaped elements, on the other hand, by nature lengthen as they are crimped and shorten as they are deployed. It may be desirable for the scaffold having the expanded or post-dilation diameter in the vessel to have the distance Z1 between segments. As stated above, during crimping initial or interim adjustments in segment spacing can be made to counteract a lengthening of segments during diameter decrease. It should be noted that, in some embodiments, during crimping Z1 does not need to be controlled or pre-set, because when deployment occurs, the coupling will lengthen to Z1 and the final deployed spacing will be Z1. This may be ideal as implants are made with a patient's leg mostly straight or in the non-compressed artery state. Any subsequent movement of the artery will then be essentially compression.

Figure 13A:
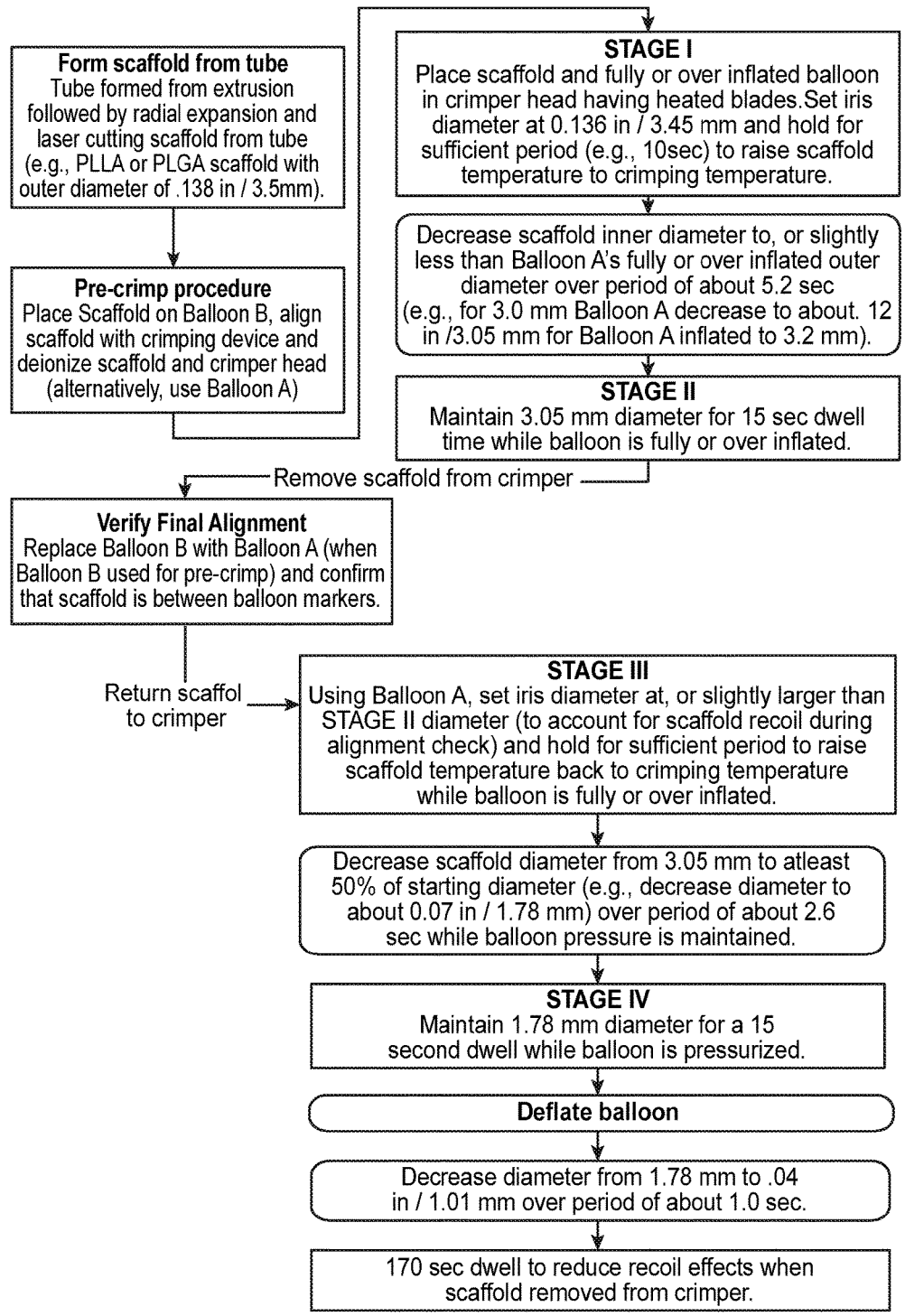
FIGS. 13A-13B are two embodiments of processes for making a medical device including crimping a scaffold to a balloon.
Figure 13B:
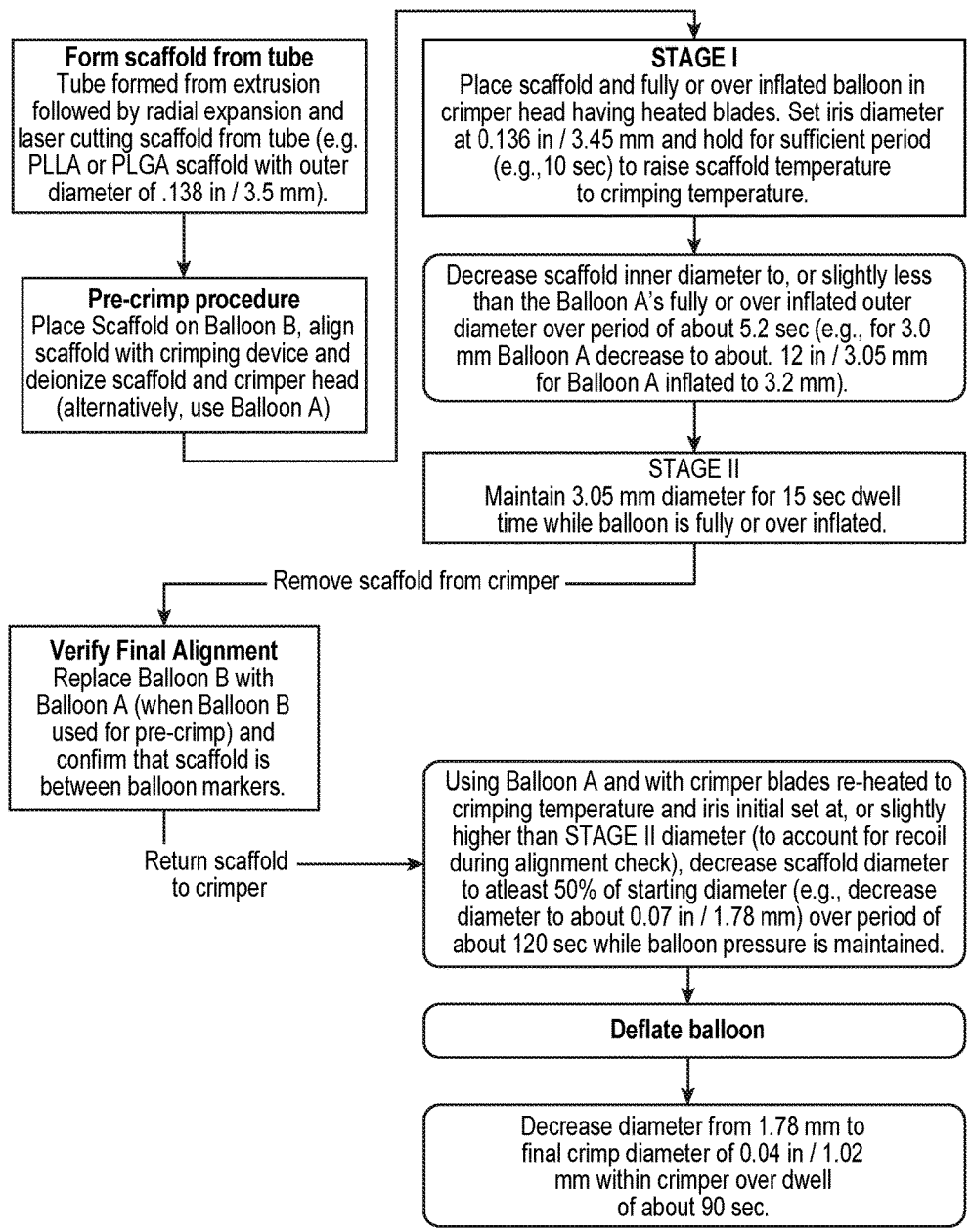

The scaffold segments may be crimped tightly on a delivery balloon using a crimping apparatus such as an iris crimper. The crimping process may include two stages, a pre-crimping process and a final crimp process. In the pre-crimp process, the diameter of the scaffold segments are reduced to a diameter between the initial diameter and the balloon diameter prior to loading the scaffold segments on the balloon. This process is illustrated in the examples of FIGS. 13A-13B.

Crimping of the scaffold, as detailed in U.S. application Ser. No. 13/194,162, includes heating the polymer material to a temperature less then, but near to the glass transition temperature of the polymer. In one embodiment the temperature of the scaffold during crimping is raised to about 5 to 15 degrees below the lower end of the glass transition temperature of the bioresorbable polymer; e.g., about 54 to 40 degrees for PLLA. When crimped to the final, crimped diameter, the crimping jaws are held at the final crimp diameter for final dwell period. This method for crimping a polymer scaffold having crush recovery is advantageous to reduce recoil when the crimp jaws are released. After the final dwell period, the scaffold is removed from the crimper and a constraining sheath is immediately placed over the scaffold to minimize recoil. Examples of such a sheath are described in U.S. application Ser. No. 13/118,311 (62571.534).

The diamond pattern disclosed herein tends to maximize the relative friction between the vessel wall and the segments. With this and the high radial and axial rigidity of the diamond pattern, endothelialization of the segments may be sped up and vessel irritation may be reduced. With rapid endothelialization, the scaffold/vessel wall becomes a composite structure which in itself enhances the radial strength and hence crush resistance of the vessel/scaffold composite. With most, if not all of the movement transferred to the gaps between the segments, the design utilizes the natural flexibility of the vessel walls to handle any compression, bending and torsional movements.

In some embodiments, a single high radial strength and stiff scaffold segment, such as described above, may be implanted at an implant site. Implanting a single segment without additional segments may be useful in treatments involving vessels that do not undergo axial compression, torsion, or bending. Examples include the Iliac and Renal artery.

During deployment at a lesion site of a conventional balloon expandable stent or scaffold, the balloons generally start to expand at the proximal and distal ends first, producing a dog bone shape. As pressure is increased, the balloon expands in the center, expanding the scaffold in the center also.

With the segmented scaffold, which can include several short scaffolds on a single balloon, the balloon can expand in a similar manner, i.e., expanding at the proximal and distal ends first, followed by expansion of a center section. Expansion at the ends first has the tendency to push the segments axially towards the center of the balloon which decreases the segment to segment gap. The gap may be decreased to the point that the segments collide with each other. This movement of the individual segments axially along the balloon during deployment, therefore, can change the segment to segment gap to an undesirably small size which can result in interference of the segments. Additionally, the segment to segment spacing will not necessarily be the same between all segments. A reduced gap or zero gap may be acceptable where non-pulsatile forces are virtually zero.

In pre-clinical animal studies, bioresorbable polymer fully disconnected segmented scaffolds have been shown to have high radial strength and fracture resistance. The sections of the artery along the segments are held open at a desired diameter. However, in some cases, the sections of the artery at the gaps between the segments are not held open to the same degree as along the segments. There appears to be "prolapse" or focal restenosis of the vessel wall inward into the artery lumen at the gaps between segments. For example, in a case where the gaps between the segments were on the order of 5 mm, prolapse or focal restenosis was observed.

Embodiments of the present invention include segmented scaffolds and delivery thereof that reduce or prevent the vessel prolapse between the segments while maintaining high radial strength and fracture resistance.

Embodiments of the present invention include deploying a segmented scaffold in such a manner that the ends of the adjacent scaffolds segments overlap or are interlinked. The segments that are overlapped or interlinked are disconnected and are not in contact. The segment ends overlap. Therefore, there is no gap between segments that is a circumferential strip or band with no support that completely encircles the vessel wall. Equivalently, there is no longitudinal position without support from a segment between the ends of adjacent segments that extends completely around the circumference of the vessel wall or scaffold.

Embodiments also include segmented scaffold segments in a crimped reduced state with ends of the adjacent scaffolds segments that overlap or are interlinked. The crimped scaffold segments can be crimped over a delivery balloon to allow balloon assisted delivery of the segments to a deployed state in a vessel. The scaffold segments are interlinked in a manner that upon expansion of the segments to a deployed state, the deployed segments are interlinked as described.

Although specific embodiments are described herein, the embodiments generally apply to segmented scaffolds made up of segments composed of struts forming a plurality of circumferential undulating rings, the undulations include peaks and valleys, as exemplified above. Undulating can refer to, but is not limited to, to a wave-like appearance or form. The wave-like appearance can be smooth, such as sinusoidal from, or jagged, such as a zigzag form. The ends of the segments, therefore, include an undulating ring also with peaks and valleys. A peak or valley undulation refers generally to the portion of an undulation or wave on either side of a peak or valley. The peak undulations project longitudinally outward or away from the end of the segment and the valley undulations extend longitudinally inward or toward the segment.

The interlinking of two adjacent scaffold segments with the above general structure is described with respect to the peak undulation and valley undulation of neighboring end rings of adjacent segments. The peak undulations of a first ring overlap or extend into the valley undulation of an adjacent ring. Likewise, the peak undulations of the adjacent ring overlap or extend into the valleys of the first ring. The degree of overlap or interlinking can be described in terms of the degree of extension of the peak undulations into the valley undulations.

The peak and valley undulations in the crimped state are compressed close to one another relative to the expanded or deployed state. The segments described are provided in the crimped state with the interlinking of the neighboring rings of adjacent segments. The degree of overlap may be greater in the crimped state than the deployed state since the degree of overlap may decrease as the segments are expanded.

Figure 8:
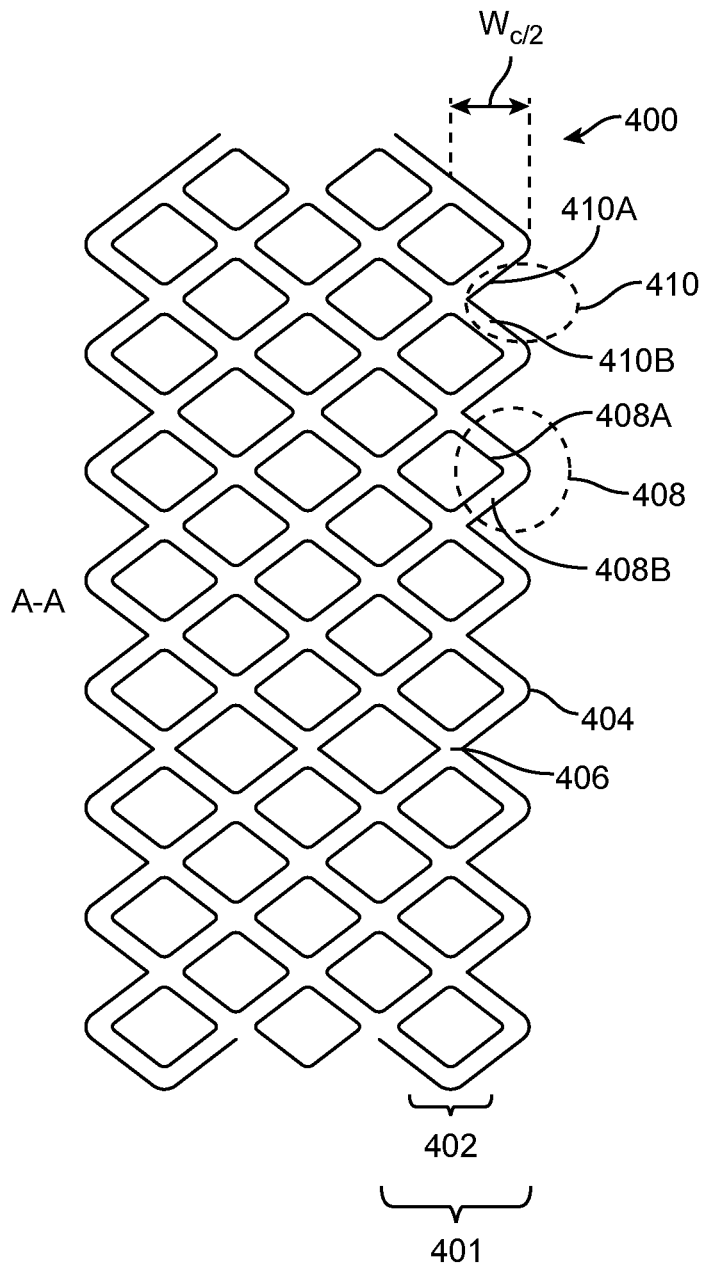
FIG. 8 illustrates a second pattern for a segment according to another aspect of the disclosure.

A scaffold having overlapping segments can be formed using the scaffolds segments described, for example, in FIGS. 7A-B. FIG. 8 depicts a flattened view of another exemplary scaffold segment 400, like segment 320 depicted in FIG. 7A. Line A-A represents the longitudinal axis of the segment. Segment 400 has an end ring 401 of diamond cells made up of two undulating rings connected at peaks, one of which is undulating end ring 402 composed of peaks 404 and valleys 406. Peak undulations 408 are composed of struts 408A and 408B which extend from two adjacent valleys and meet at a peak. Valley undulations 410 are composed of struts 410A and 410B which extend from two adjacent peaks and meat at a valley. Peak undulations project longitudinally outward from the segment and valley undulations extend longitudinally inward into the segment. The Z-axis dimension, height or length of the valley and peak undulations is one half the longitudinal width of a diamond, Wc/2, which can be an LMD for a coupling for segment 400 with an adjacent segment 400. In such an example an end ring of a first segment 400 may have peak or crest aligned with corresponding valley or trough with the coupling extending from the trough of the one segment to peak of the other segment. One or two couplings spaced by 180 degrees would be the only structures connecting the two segments.

Figure 9:
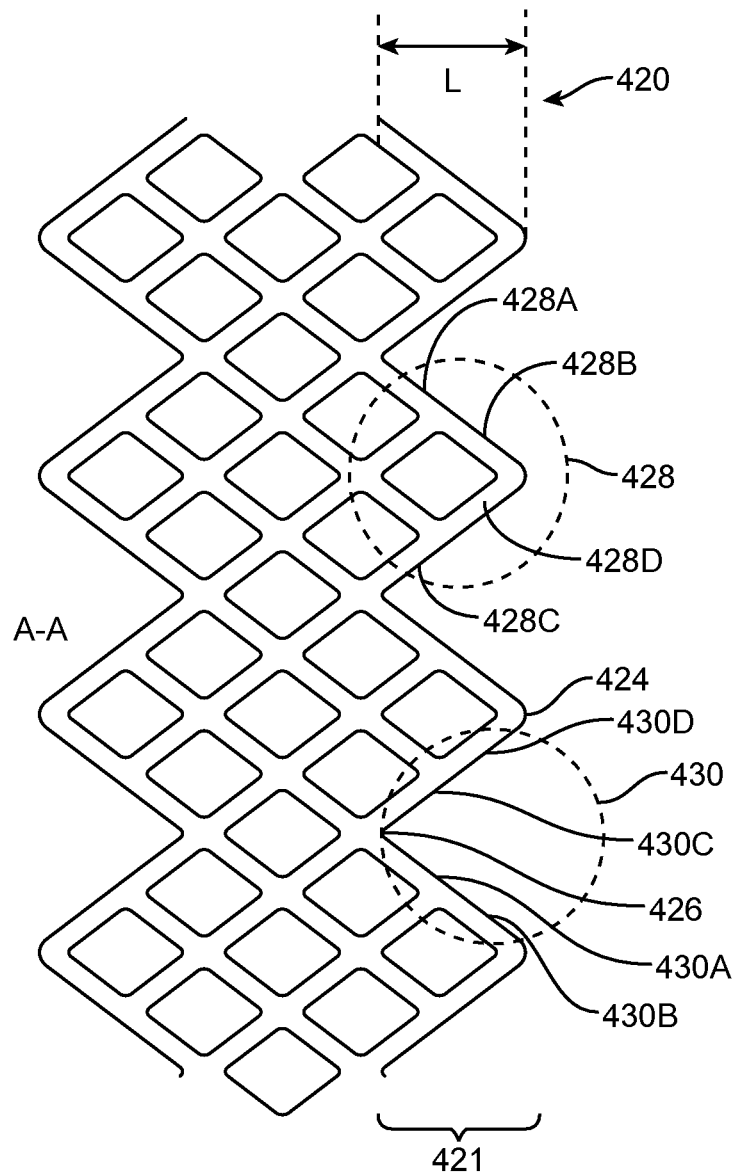
FIG. 9 illustrates a third pattern for a segment according to another aspect of the disclosure.

FIG. 9 depicts an exemplary segment 420 based on segment 400 of FIG. 8 in which alternating diamonds are omitted at each end. Equivalently, every other peak undulation is omitted on both ends of the segment. Specifically, every other pair of struts 408A and 408B are omitted. In addition, the diamonds that are omitted at opposite ends are longitudinally aligned or opposite from one another or "in-line" diamonds are omitted. Thus, the embodiment in FIG. 8 will be referred to as an "in-line segment." The modified segment, therefore, has an end ring with an undulating, zigzag structure in which the length of a "zig" and "zag" or from a valley to a peak is twice the length of a side of a diamond of a diamond cell. The longitudinal length of a peak or valley undulation is the longitudinal length of a diamond cell.

As shown in FIG. 9, segment 420 has an undulating end ring 421 composed of peaks 424 and valleys 426. Peak undulations 428 are composed of pairs of in-line struts, (428A, 428B) and (428C, 428D) which extend from two adjacent valleys and meet at a peak. Valley undulations 430 are composed of pairs of in-line struts (430A, 430B) and (430C, 430D) which extend from two adjacent peaks to a valley. Each of the two inline struts is the length of a side of the diamond cells. The length "L" in FIG. 9 can be a LMD for a coupling extending from trough 426 to a peak 424 of an adjacent segment 420, or a LMD extending from a peak of one to a peak of the adjacent segment 420.

Figure 10:
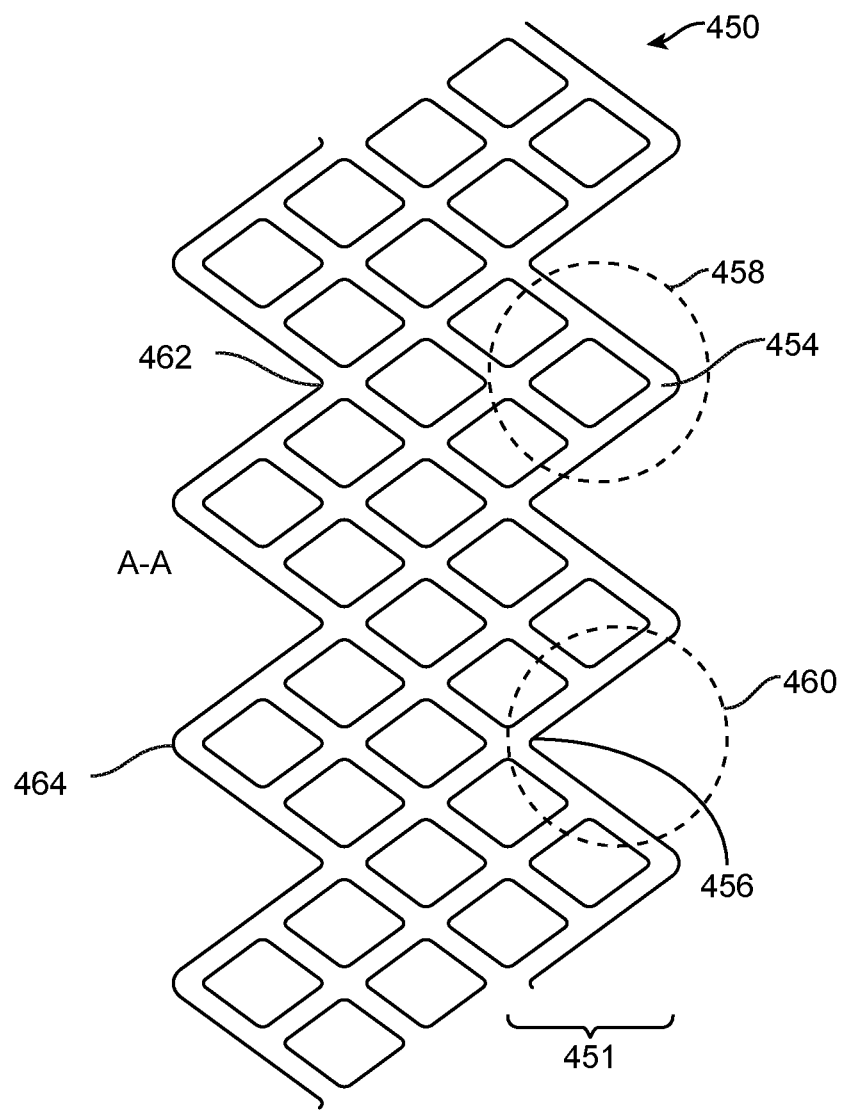
FIG. 10 illustrates a fourth pattern for a segment according to another aspect of the disclosure.

FIG. 10 depicts an exemplary segment 450 based on segment 400 of FIG. 8 in which alternating diamonds are omitted at both ends of the segment. Specifically, every other pair of struts 408A and 408B is omitted. Segment 450 differs from segment 420 of FIG. 8 in that omitted diamonds at one end are not longitudinally aligned with omitted diamonds at the other end. The diamonds omitted at one end are circumferentially off-set by one diamond cell. The embodiment in FIG. 10 will be referred to as an "off-set segment." An alternate embodiment is omitted diamonds every third or every fourth diamond around the circumference of the end ring.

As shown in FIG. 10, segment 450 has an undulating end ring 451 composed of peaks 454 and valleys 456. Peak undulations 458 are composed of two pairs of in-line struts, as described in FIG. 9, which extend from two adjacent valleys and meet at a peak. Valley undulations 460 are composed of pairs of inline struts, as described in FIG. 9, which extend from adjacent peaks to a valley. Peak undulations project longitudinally outward from the segment and valley undulations extend longitudinally inward into the segment. The length 451 (or about the Z-axis width of the diamond shaped cell) in FIG. 10 can be a LMD for a coupling extending from trough 456 to a peak 454 of an adjacent segment 450, or a LMD extending from a peak of one to a peak of the adjacent segment 450.

Figure 11:
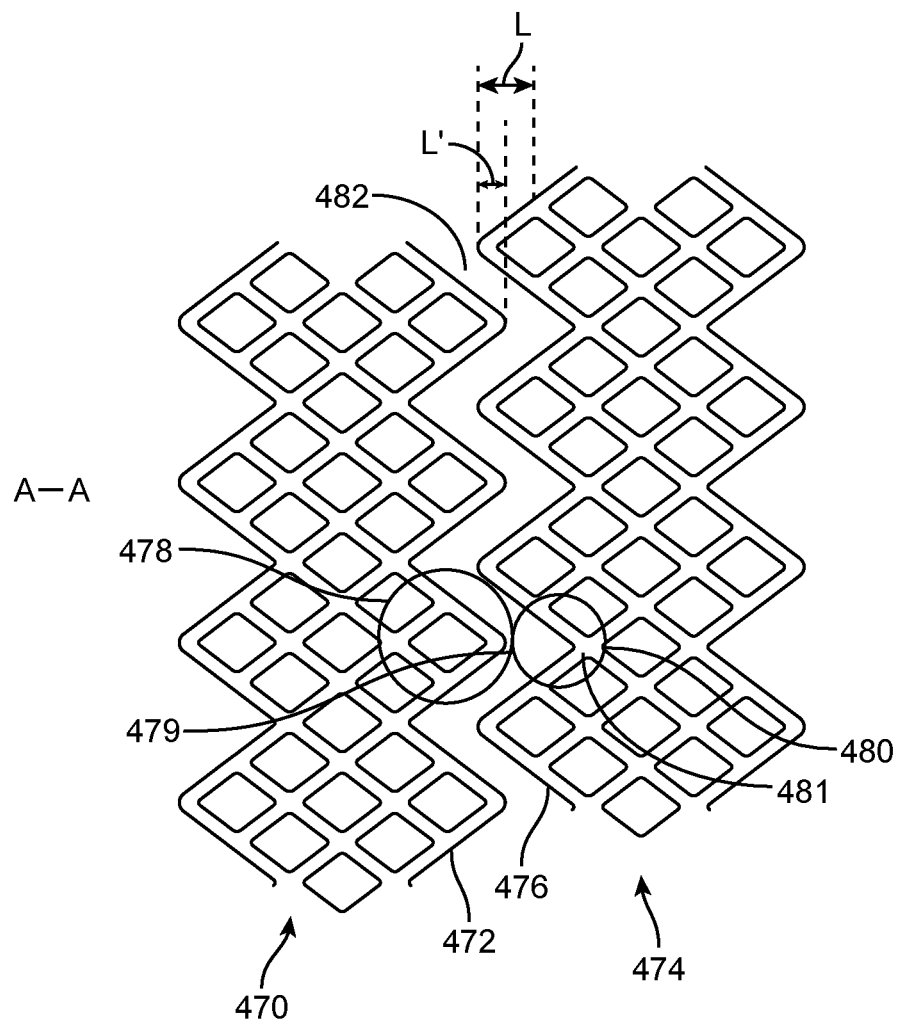
FIG. 11 illustrates a pair of segments according to FIG. 10 disposed adjacent each other.
Figure 12:
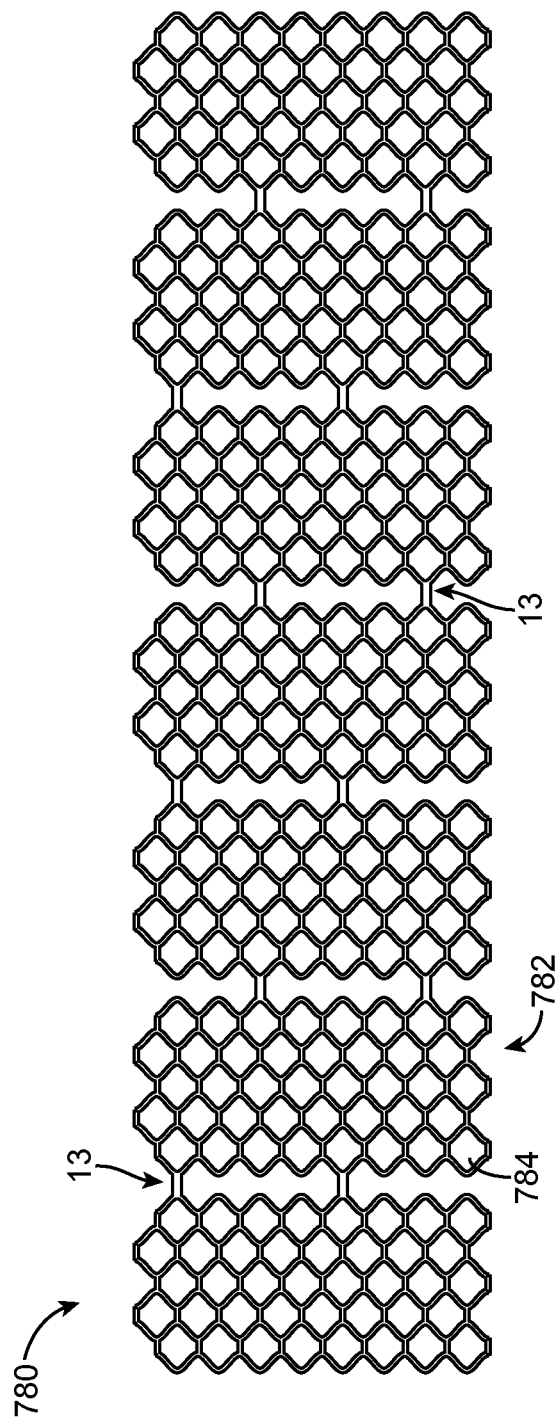
FIG. 12 illustrates a scaffold including seven segments joined by couplings.

FIG. 11 depicts two in-line segments 470 and 474 which are joined by a pair of couplings c400, each of which provide z1=L, which may be equal to, or greater than the LMD, depending on the coupling used (as explained below in connection with FIGS. 3-6). In this arrangement the couplings c400 connect between a trough and crest. In this arrangement there is overlap such that the peak 458 (having length of about 451) becomes nested within troughs 460. Alternatively the coupling c400 can connect between adjacent peaks 458, in which case there is no nesting or overlap. As shown the trough and peak are longitudinally aligned with the coupling c400 extending therebetween. For the coupling's joint permitting rotation about the X axis the trough portion of the coupling c400 connection become circumferentially offset from the peak portion.

As shown in FIG. 11, there is a gap 482 between end rings 472 and 476 of segments 470 and 474, respectively. However, the gap has an undulating profile that follows the interlinking profile of end rings 472 and 476. As a result, there is no longitudinal position completely around a vessel wall that is not supported.

In order for deployed segments to have overlap, the couplings are connected with an LMD that preserves a degree of overlap even when the scaffold segments are located at the Z1 distance from each other. According to this aspect of the disclosure, a scaffold includes a first scaffold segment connected to a second scaffold segment only by one or more couplings where there is overlapping of the segments when the segments are a maximum axial distance from each other, i.e., the axial or Z-axis distance from each other is Z1, and each of the couplings' LMD is equal to or less than Z1.

The scaffold segments of the present invention can be made from variety of biodegradable polymers including, but not limited to, poly(L-lactide) (PLLA), polymandelide (PM), poly(DL-lactide) (PDLLA), polyglycolide (PGA), polycaprolactone (PCL), poly(trimethylene carbonate) (PTMC), polydioxanone (PDO), poly(4-hydroxy butyrate) (PHB), and poly(butylene succinate) (PBS). The scaffold segments can also be made from random and block copolymers of the above polymers, in particular, poly(L-lactide-co-glycolide) (PLGA) and poly(L-Lactide-co-caprolactone) PLLA-PCL. The scaffold can also be made of a physical blending of the above polymers. The scaffold segments can be made from PLGA including any molar ratio of L-lactide (LLA) to glycolide (GA). In particular, the stent can be made from PLGA with a molar ratio of (LA:GA) including 85:15 (or a range of 82:18 to 88:12), 95:5 (or a range of 93:7 to 97:3), or commercially available PLGA products identified as having these molar ratios. High strength, semicrystalline polymers with a Tg above body temperature include PLLA, PGA, and PLGA.

Embodiments of the invention further may include couplings joining scaffold segments, methods of making or methods of crimping such segments as described in U.S. application Ser. No. 13/584,678. It will be understood that use of the word "linkage" herein refers specifically and exclusively to the coupling's feature (as stated earlier) of having or providing, among other things, a joint defining a DOF including at least in the Z-axis translation direction. This is different from use of the word "link" or "connecting links" as those terms simply describe a connection without having or defining a DOF or joint in the structure.

The width and/or radial thickness of struts of a scaffold may be 80 to 400 microns, or more narrowly, 100 to 250 microns, 140 to 180 microns, 200 to 400 microns, 140 to 160 microns, or 300 to 350 microns. The thickness and width can be different. For example, the width can be at or about 350 microns (e.g., ±10 microns) and the thickness can be at or about 300 microns (e.g., ±10 microns).

Semi-crystalline polymers such as poly(L-lactide) (PLLA) with glass transition temperature (Tg) above human body temperature may be suitable as materials for a totally bioresorbable scaffold since they are relatively stiff and strong at the conditions of the human body. However, they tend to be brittle at these conditions. These polymer systems exhibit a brittle fracture mechanism in which there is little plastic deformation prior to failure. As a result, a stent fabricated from such polymers can be vulnerable to fracture during fabrication and use of a scaffold, i.e., crimping, delivery, deployment, and during a desired treatment period post-implantation.

Embodiments of the present invention are applicable to endovascular treatment of coronary and peripheral disease in coronary arteries and various peripheral vessels including the superficial femoral artery, the iliac artery, and carotid artery. The embodiments are further applicable to various stent types, such as self-expandable and balloon expandable stents. The embodiments are further applicable to various stent designs including scaffolding structures formed from tubes, wire structures, and woven mesh structures. Embodiments also applicable to different materials that are permanent implants such as polymers and metals like Nitinol, Egeloy, stainless steel and cobalt chrome.

In general, the initial clinical need for a bioresorbable scaffold is to provide mechanical/structural support to maintain patency or keep a vessel open at or near the deployment diameter. The scaffold is designed to have sufficient radial strength or vessel wall support for a period of time. The vessel wall support provided by the scaffold allows the segment of the vessel to undergo healing and remodeling at the increased diameter. Remodeling refers generally to structural changes in the vessel wall that enhance its load-bearing ability.

A period of vessel wall support is required in order to obtain permanent positive remodeling and vessel healing and hence maintenance of vessel patency. As the polymer of the scaffold degrades, the radial strength of the scaffold decreases and the load of the vessel is gradually transferred from the scaffold to the remodeled vessel wall. In addition to the decline in radial strength, the degradation of the scaffold also causes a gradual decline in the mechanical integrity, i.e., connectivity of struts and the size and shape of the overall scaffold structure. The struts gradually resorb and disappear from the vessel.

As discussed earlier, the amount of movement experienced by a peripheral scaffold in the peripheral artery is greater than what a coronary scaffold experiences in the coronary artery. A peripheral scaffold can be subjected to a high degree of flexing, axial elongation/compression, pinching, bending, and torsion after implantation. Axial stresses on the scaffold can arise from the axial compression and extension, flexural stresses are imposed by lateral flexing, and crushing forces are imparted by pinching, while helical stress can arise from torsional forces. Resulting stresses are propagated along the length of the scaffold and can impart significant forces throughout the scaffold structure. When the load-path for the equilibrating axial forces are present in the scaffold structure, the axial forces can cause failure in ring struts, resulting in a decrease or loss in vessel wall support provided by the scaffold. According to the disclosure, for a limited range of axial movement the axial load transmission to a ring, as might induce significant bending loads at a crown, the LMD provided by the coupling can reduce the loading over time. It is of chief interest to reduce the amount of loading that contribute to fatigue failure.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A scaffold, comprising:
   a first segment comprising a polymer and having a pattern comprising:
      a first ring, a second ring and a third ring,
      a peak of the first ring is adjoined with a valley of the second ring,
      a peak of the second ring is adjoined with a valley of the third ring,
      a plurality of diamond shape cells are formed by the adjoined first and second rings and by the adjoined second and third rings, and
      the first ring is an end ring composed of struts forming peak and valley undulations and the length of a peak or valley undulation is equal to a width of, or one half the width of a diamond shape cell;
   a second segment comprising the polymer; and
   a mechanical connection comprising at least one coupling having a lost motion distance (LMD) and a maximum axial distance (Z1);
   wherein the first segment and the second segment are joined to each other by only the coupling; and
   wherein the LMD is at least four times the width of the diamond shape cell to account for changes in a length of the segments when expanded from a crimped state by a balloon.

2. The scaffold of claim 1, wherein the first and second segments are laser cut from a tube comprising poly(L-lactide).

3. The scaffold of claim 1, wherein the coupling is one of a male-female coupling, a pin and socket coupling, a flexible band coupling, or a stiff band coupling.

4. The scaffold of claim 3, wherein the coupling is a flexible coupling including a hook and a loop.

5. The scaffold of claim 1, wherein the LMD or Z1 is equal to about 7% to about 10% of a length of the first segment to account for an expected 7% to about 10% axial compression of the first segment when the first segment is implanted in a vessel.

6. The scaffold of claim 5, wherein the coupling is one of a male and female connector, a flexible band, a stiff band, and a pin received in a slot.

7. The scaffold of claim 1, wherein the coupling is a beam, string or thread; and wherein when the coupling is a thread or string, the string or thread joins together one pair of adjacent peaks of the segments, or a plurality of pairs of adjacent peaks.

8. The scaffold of claim 1, wherein the coupling comprises a first portion integrally formed with the first segment, a second portion integrally formed with the second segment, and a connection formed between the first and second portion and defining the LMD.

9. A medical device, comprising:
   the scaffold of claim 1 crimped to a balloon, the scaffold having a crimped state, wherein the scaffold is made from a tube comprising poly(L-lactide) and the scaffold is plastically deformed when expanded from the crimped state by the balloon;
   wherein the scaffold has an outer, expanded diameter;
   wherein the scaffold has a crimped diameter; and
   wherein the expanded diameter is at least 2, 3, or 3.5 times larger than the crimped diameter, or the balloon nominal inflation diameter is at least 2.5 times the crimped diameter.

10. The medical device of claim 9, wherein the crimped first and second segments are arranged such that the first segment is separated from the second segment by a maximum or minimum axial distance, and the maximum or minimum distance is defined by the coupling.

11. The scaffold of claim 9, wherein the coupling is one of a male-female coupling, a pin and socket coupling, a flexible band coupling, or a stiff band coupling.

12. The scaffold of claim 11, wherein LMD accounting for displacement of the first segment relative to the second segment when implanted in a vessel is equal to about $$\tfrac{1}{2} \times D \times \mathrm{TAN}(\Phi),$$

where D is the outer, expanded diameter and $\Phi$ is between 10 and 30 degrees.

13. The scaffold of claim 11, wherein the LMD or Z1 is equal to about 7% to about 10% of the first segment length to account for an expected 7% to about 10% axial compression of the first segment when the first segment is implanted in a vessel.

14. The scaffold of claim 1, wherein the first segment further includes a second end ring composed of struts forming undulating peaks and valleys, wherein a peak of the first end ring is longitudinally aligned with a peak of the second end ring.

15. The scaffold of claim 1, wherein LMD is equal to Z1.

16. A scaffold, comprising:
a first segment comprising a polymer and having a first end ring forming peaks and valleys, wherein a peak is separated from a valley by an axial distance (L);
a second segment comprising the polymer and having a second end ring forming peaks and valleys, wherein a peak is separated from a valley by L; and
a mechanical connection comprising at least one coupling having a lost motion distance (LMD) and a maximum axial distance (Z1);
wherein the first segment and the second segment are joined to each other at the respective first and second end rings by only the coupling;
wherein the coupling extends from a valley of the first end ring to a peak of the second end ring; and
wherein the LMD is less than or equal to L, such that the first and second end rings are configured to overlap each other.

17. The scaffold of claim 16,
wherein at least one of the first segment and the second segment has a pattern, the pattern comprising:
more than two rings, and
diamond shape closed spaces having circumferentially aligned vertices and formed by adjoined rings.

18. The scaffold of claim 17, wherein L is equal to ½ of, or a width of the diamond shape.

19. The scaffold of claim 17, wherein Z1 is equal to at least ½ a width of the diamond shape.

20. A scaffold, comprising:
a first segment comprising a polymer and having a pattern comprising more than two rings adjoined to each other, wherein adjoined rings form a diamond shape cell having a diamond width;
a second segment comprising the polymer; and
a mechanical connection comprising at least one coupling having a lost motion distance (LMD) and a maximum axial distance (Z1);
wherein the first segment and the second segment are joined to each other by only the coupling; and
wherein the LMD accounts for displacement of the first segment relative to the second segment, such that when implanted in a vessel the LMD is equal to about ½ D (TAN($\Phi$)), where D is an outer expanded diameter of the scaffold and $\Phi$ is between 10 and 30 degrees.

21. The scaffold of claim 20, wherein the coupling is a beam, string or thread, and wherein when the coupling is a thread or string, the string or thread joins together one pair of adjacent peaks of the segments, or a plurality of pairs of adjacent peaks.

22. The scaffold of claim 20, wherein the coupling comprises a first portion integrally formed with the first segment, a second portion integrally formed with the second segment, and a connection formed between the first and second portion and defining the LMD.

* * * * *